US011882816B2

(12) United States Patent
Wang et al.

(10) Patent No.: US 11,882,816 B2
(45) Date of Patent: Jan. 30, 2024

(54) GENETICALLY ENGINEERED NON-HUMAN MAMMAL, CONSTRUCTION METHOD THEREFOR AND USE THEREOF

(71) Applicant: Miao Wang, Beijing (CN)

(72) Inventors: Miao Wang, Beijing (CN); Hong Chen, Beijing (CN)

(73) Assignee: Miao Wang, Beijing (CN)

( * ) Notice: Subject to any disclaimer, the term of this patent is extended or adjusted under 35 U.S.C. 154(b) by 818 days.

(21) Appl. No.: 16/609,110

(22) PCT Filed: Apr. 28, 2018

(86) PCT No.: PCT/CN2018/085097
§ 371 (c)(1),
(2) Date: Oct. 28, 2019

(87) PCT Pub. No.: WO2018/196874
PCT Pub. Date: Nov. 1, 2018

(65) Prior Publication Data
US 2020/0077632 A1 Mar. 12, 2020

(30) Foreign Application Priority Data
Apr. 28, 2017 (CN) .......................... 201710292460.X

(51) Int. Cl.
A01K 67/027 (2006.01)
C12N 15/90 (2006.01)

(52) U.S. Cl.
CPC .......... A01K 67/0276 (2013.01); C12N 15/90 (2013.01); C12N 2310/20 (2017.05); C12N 2517/02 (2013.01); C12N 2800/107 (2013.01); C12N 2800/60 (2013.01)

(58) Field of Classification Search
None
See application file for complete search history.

(56) References Cited

U.S. PATENT DOCUMENTS

2005/0136005 A1  6/2005  Kozarsky et al.
2008/0075663 A1  3/2008  Raffai et al.

FOREIGN PATENT DOCUMENTS

CN  106399366 A  2/2017

OTHER PUBLICATIONS

Dolatshad et al. Mammalian Genome 26:598-608, 2015 (Year: 2015).*
Ledford. Nature 583:17-18, 2020 (Year: 2020).*
Schaefer et al. Nat Methods 14(4) 547-547, 2017. Author Manuscript pp. 1-3 (Year: 2017).*
Lee & Kim Nature Biotechnology Advanced Online Publication. doi:10.1038/nbt.4207. 2018. pp. 1-2 (Year: 2018).*
Kocher et al. (Biochim Biophys Acta 1782(5):310-316:2008) (Year: 2008).*
International Search Report with English translation and Written Opinion in corresponding International Application No. PCT/CN2018/085097, dated Aug. 7, 2018, 10 pages.
Min Xu, et al., "The establishment of atherosclerosis model in apolipoprotein E-deficient rats", Chinese Journal of Arteriosclerosis, vol. 25, No. 1, Jan. 31, 2017, pp. 78-82, ISSN: 1007-3949, with English abstract.
Ayce Yesilaltay, et al. "Loss of PDZK1 Causes Coronary Artery Occlusion and Myocardial Infarction in Paigen Diet-Fed Apolipoprotein E Deficient Mice", Plos One, vol. 4, No. 12, Dec. 1, 2009, pp. 1-7, ISSN: 1932-6203.
Andrew Plump, et al. "Severe Hypercholesterolemia and Atherosclerosis in Apolipoprotein E-Deficient Mice Created by Homologous Recombination in ES Cells", Cell, vol. 71, Oct. 16, 1992, pp. 343-353.
Attilio Rigotti, et al. "A targeted mutation in the murine gene encoding the high density lipoprotein (HDL) receptor scavenger receptor class B type I reveals its key role in HDL metabolism", Proceedings of the National Academy of Sciences of the United States of America, vol. 94, Nov. 1997, pp. 12610-12615.
Nicolás Santander, et al. "Developmental abnormalities in mouse embryos lacking the HDL receptor SR-BI", Human Molecular Genetics, vol. 22, No. 6, Dec. 5, 2012, pp. 1086-1096.
Anne Braun, et al. "Loss of SR-BI Expression Leads to the Early Onset of Occlusive Atherosclerotic Coronary Artery Disease, Spontaneous Myocardial Infarctions, Severe Cardiac Dysfunction, and Premature Death in Apolipoprotein E- Deficient Mice", Circulation Research, Journal of the American Heart Association, vol. 90, Jan. 3, 2002, pp. 270-276.
John Cha, et al. "Evolution of angiotensin II-mediated atherosclerosis in ApoE KO mice", Molecular Medicine Reports, vol. 3, 2010, pp. 565-570.
Chi Dae Kim, et al. "Endogenous angiotensin II enhances atherogenesis in apoprotein E-deficient mice with renovascular hypertension through activation of vascular smooth muscle cells", Life Sciences, vol. 80, 2007, pp. 1057-1063.
Yi Chu, et al. "Fibrotic Aortic Valve Stenosis in Hypercholesterolemic/Hypertensive Mice", Arteriosclerosis, Thrombosis, and Vascular Biology, vol. 36, 2016, pp. 466-474.
Mengcheng Shen, et al. "Divergent Roles of Matrix Metalloproteinase 2 in Pathogenesis of Thoracic Aortic Aneurysm", Arteriosclerosis, Thrombosis, and Vascular Biology, vol. 35, 2015; pp. 888-898.
Dimitris Tousoulis, et al. "Inflammatory cytokines in atherosclerosis: Current therapeutic approaches", European Heart Journal, vol. 37, 2016, pp. 1723-1732.

* cited by examiner

Primary Examiner — Marcia S Noble
(74) Attorney, Agent, or Firm — Maier & Maier, PLLC

(57) ABSTRACT

The present invention relates to genetically engineered non-human mammal and cells, organs and tissues; to use thereof in medicinal and disease research; to a method for producing non-human animals and cells, organs and tissues; and to a method for researching in medicine and disease by virtue of the non-human mammals or cells, organs or tissues.

9 Claims, 16 Drawing Sheets
Specification includes a Sequence Listing.

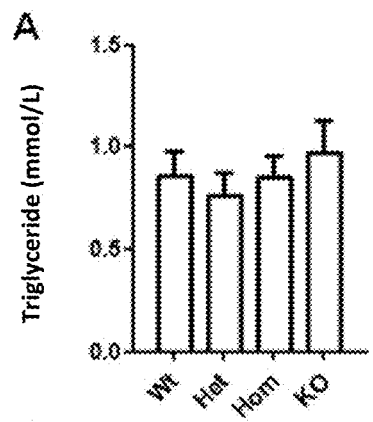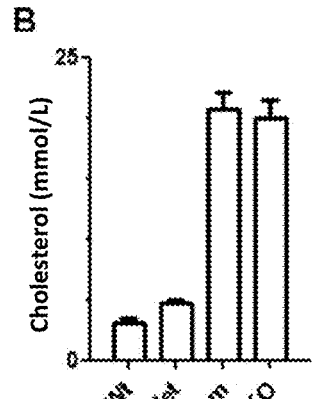
Figure 5A  Figure 5B
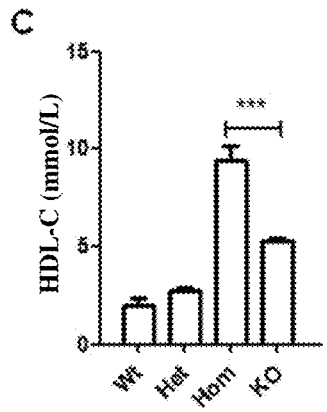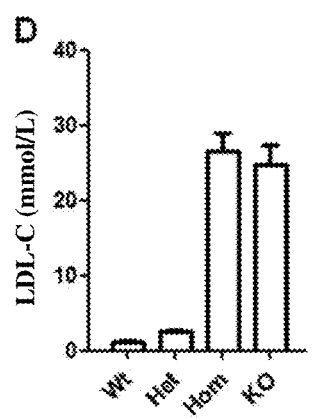
Figure 5C  Figure 5D
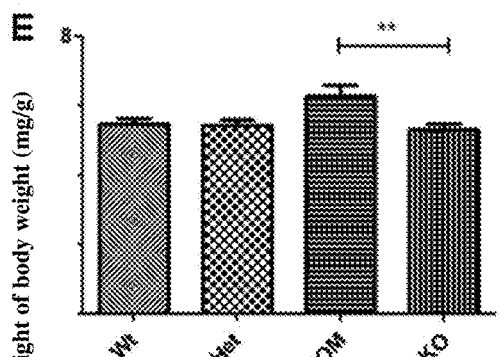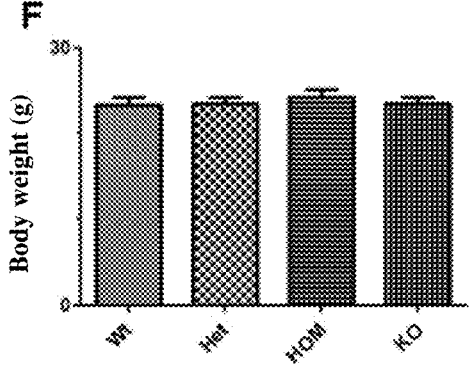
Figure 5E  Figure 5F
Figure 5

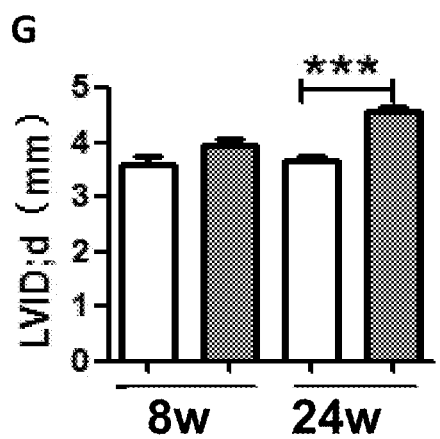
Figure 5G
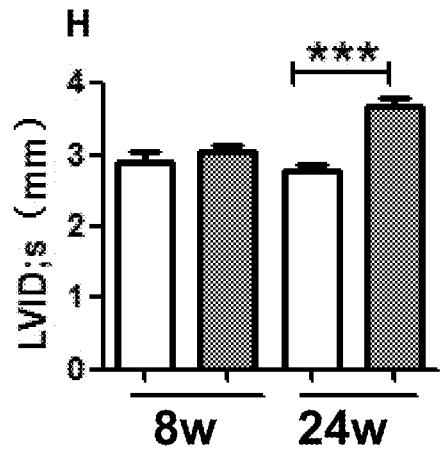
Figure 5H
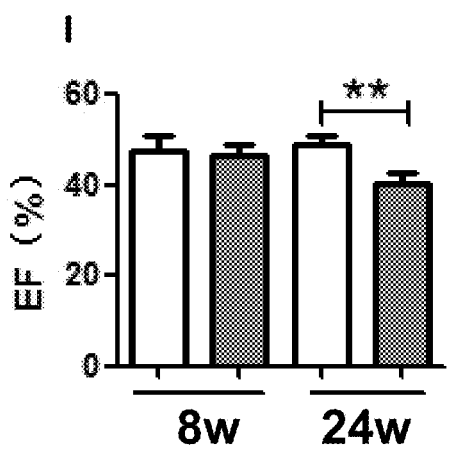
Figure 5I
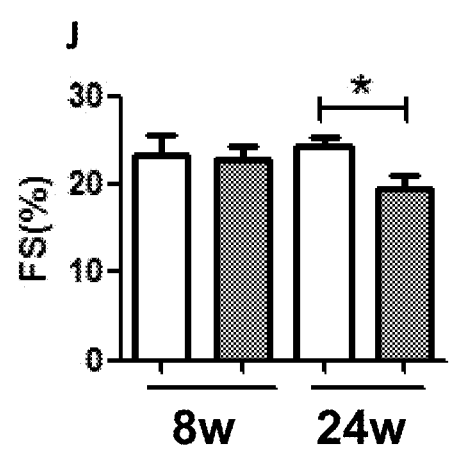
Figure 5J
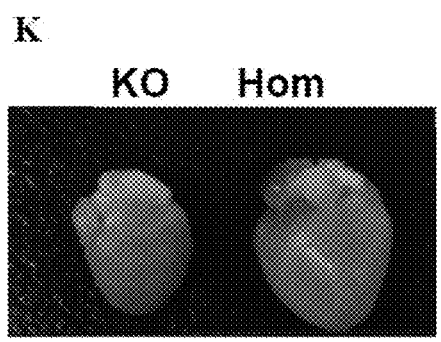
Figure 5K
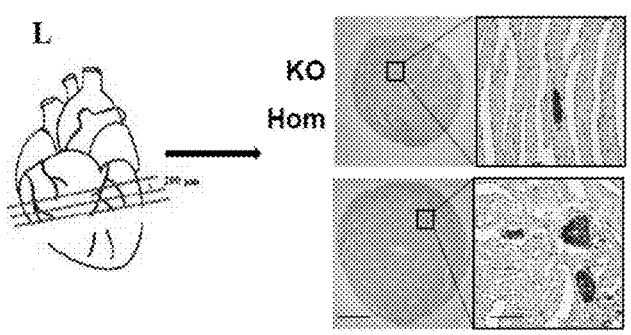
Figure 5L
Figure 5

SEQUENCE LISTING

<160> NUMBER OF SEQ ID NOS: 15

<210> SEQ ID NO 1
<211> LENGTH: 1040
<212> TYPE: DNA
<213> ORGANISM: Artificial Sequence
<220> FEATURE:
<223> OTHER INFORMATION: intron

<400> SEQUENCE: 1

```
aatgaggtgt ccgctccctt tgttggcggg ggaggggagc gggggtcac aaggcatcca      60 aactccacct ctttcctctg ccctgctgtg aaggggagga gaacaacccg cctcgtgaca     120
gggggctggc acagcccgcc ctagccctga ggaggggggcg ggacaggggg agtcctataa    180
```

```
ttggaccggt ctgggatccg atcccctgct cagaccctgg aggctaagga cttgtttcgg    240
aaggagctgg taagacaagc tgggctgggg attcacccag gaccttggt aggatgtggg     300 ctgggaacct tgagatcccc cggagtccag gaaacaggca caagaattgg aaaagcaggc    360
agcacgatag aagtcttggg ggacaaacta aggactcgag gtaactagcc tttgccagag    420
tcagagcagg tggaggggtt acctccagga aggagtacgg gactgtcggt gcacggcgta    480
ccggctcaac taggaaccat cctatggcga aagaagttcc tattctctag aaagtatagg    540
aacttcaaac tcgggatgag ccttaggctg cttttatata aatacctact gatttccatc    600
acagtcccca gtaacccgg actggtttca aactgtggct cctcatggct gagctcccta     660
agttctgtag ttgtgggagg gtaccacttc gcagggatgg aggacgatta aaaatcgtgt    720
taaattaaca caaatggaa agcaggactt agccggaag aaagaggaat gtaagctgga      780
ccacccgctg gccctctgtg aagtggaatt tgaaccctag gagagggagc tggaatttt     840 ggcagcggat ccaccccggg gtgccgagat agcgaactcg gcaaggggag gtaaacagac    900 cttttgggaag agcgggtgct ctgttttgga gatgtttgtg atggctcaca gatctgagaa   960
gggaagatgg ggttctctgg gtggccggag tccctccacc ccgcccct ggtgttcaaa     1020 gacaatttttt ccctccgcag                                              1040

<210> SEQ ID NO 2
<211> LENGTH: 23
<212> TYPE: DNA
<213> ORGANISM: Artificial Sequence
<220> FEATURE:
<223> OTHER INFORMATION: exon

<400> SEQUENCE: 2
actggccaat cacaattgcg aag                                             23

<210> SEQ ID NO 3
<211> LENGTH: 372
<212> TYPE: DNA
<213> ORGANISM: Artificial Sequence
<220> FEATURE:
<223> OTHER INFORMATION: CDS

<400> SEQUENCE: 3
atggcctcca ccttcaaccc cagagagtgt aaattgtcca acaagagggg gcagaactat     60
ggcttctttc tccgaattga aaggacact gatggtcacc tgatccgggt gattgaggag     120
gggagcccag cagagaaggc gggctcctg gacggtgaca gggtgctcag gatcaatggt     180
gtctttgtcg acaaggagga gcatgcgcag gtggtggagc tggtcagaaa gagtgggaat    240
tcagtgactc tgctggtcct ggatggagac tcctatgaga aggctgtgaa aaatcaggtg    300
gatttgaaag agctggatca aagccagagg gaggccgctc tgaatgatta caaggatgac    360
gacgataagt aa                                                        372

<210> SEQ ID NO 4
<211> LENGTH: 134
<212> TYPE: DNA
<213> ORGANISM: Artificial Sequence
<220> FEATURE:
<223> OTHER INFORMATION: CDS

<400> SEQUENCE: 4
cctggaggct tgctgaaggc tgtatgctga ataatcgatc ttgctgagtc gttttggcca     60
```

```
ctgactgacg actcagcgat cgattattca ggacacaagg cctgttacta gcactcacat    120
ggaacaaatg gccc                                                      134

<210> SEQ ID NO 5
<211> LENGTH: 718
<212> TYPE: DNA
<213> ORGANISM: Artificial Sequence
<220> FEATURE:
<223> OTHER INFORMATION: CDS

<400> SEQUENCE: 5
ttcattttat gtttcaggtt caggggagg tgtgggaggt ttttaaagc aagtaaaacc       60 tctacaaatg tggtatggct gattatgatc ctctagacat atgttagaag gggtggatgt   120
atacgcggtc cctctttctt cgggcaggct tggccacctc atggtcgccg ccggcccct    180 tgatcttgtc cacctggccc tggatcttgc tggcaaaggt cgcacagcgt tgcggcagcc   240
acttcttgag caggtcagaa cactgcacgt tggcaagccc tttgaggcag ccagttgtgc   300
agtccacaca cagatcgacc tgtgcgatga actgctccat gggctccaag tccttgaacc   360
caggaatctc aggaatgtcg acgatcgcct cgcctatgcc gccctgtgcg gactctttgt   420
cgccttcgta ggtgtggcag cgtcctggga tgaacttctt catcttgggc gtgcacttga   480
tgtgggacag gcagatcaga cagccctgg tgcagccagc tttccgggca ttggcttcca   540
tctctttgag cacctccagc ggcagcttct tgccgggcaa cttcccgcgg tcagcatcga   600
gatccgtggt cgcgaagttg ctggccacgg ccacgatgtt gaagtcttcg ttgttctcgg   660
tgggcttggc ctcggccaca gcgatgcaga tcagggcaaa cagaactttg actcccat    718

<210> SEQ ID NO 6
<211> LENGTH: 395
<212> TYPE: DNA
<213> ORGANISM: Artificial Sequence
<220> FEATURE:
<223> OTHER INFORMATION: exon

<400> SEQUENCE: 6
caagggctgg ttcgagccaa tagtggaaga catgcatcgc cagtgggcaa acctgatgga    60
gaagatacag gcctctgtgg ctaccaaccc catcatcacc ccagtggccc aggagaatca   120
atgagtatcc ttctcctgtc ctgcaacaac atccatatcc agccaggtgg ccctgtctca   180
agcacctctc tggccctctg gtggcccttg cttaataaag attctccgag cacattctga   240
gtctctgtga gtgattccaa tcagcttcag cctcagttta ttgtttttg ccttacctag    300 cacacattcc atggccctgt cactatctgt agagggaggt ggttttgcag caatagaaat   360
gaagcctagg acctagcaac ataaaagaac aagtg                              395

<210> SEQ ID NO 7
<211> LENGTH: 167
<212> TYPE: DNA
<213> ORGANISM: Artificial Sequence
<220> FEATURE:
<223> OTHER INFORMATION: exon

<400> SEQUENCE: 7
atctaccact gagccacgcc cacagcccct cactgggga ttctaggcag gggctctacc     60
actgagccac ccgcagcccc tcactgggga atcatatcta ccactgagtc acgcccctcc   120
agcccctcac tacgggaatt ctagtcagta gctctaccac tgagcca                 167
```

<210> SEQ ID NO 8
<211> LENGTH: 3415
<212> TYPE: DNA
<213> ORGANISM: Artificial Sequence
<220> FEATURE:
<223> OTHER INFORMATION: CDS

<400> SEQUENCE: 8

| | |
|---|---|
| catggcctcc accttcaacc ccagagagtg taaattgtcc aaacaagagg ggcagaacta | 60 |
| tggcttcttt ctccgaattg agaaggacac tgatggtcac ctgatccggg tgattgagga | 120 |
| ggggagccca gcagagaagg cggggctcct ggacggtgac agggtgctca ggatcaatgg | 180 |
| tgtctttgtc gacaaggagg agcatgcgca ggtggtggag ctggtcagaa agagtgggaa | 240 |
| ttcagtgact ctgctggtcc tggatggaga ctcctatgag aaggctgtga aaaatcaggt | 300 |
| ggatttgaaa gagctggatc aaagccagag ggaggccgct ctgaatgatg attacaagga | 360 |
| tgacgacgat aagtaacctg gaggcttgct gaaggctgta tgctgaataa tcgatcttgc | 420 |
| tgagtcgttt tggccactga ctgacgactc agcgatcgat tattcaggac acaaggcctg | 480 |
| ttactagcac tcacatggaa caaatggccc ctgtgccttc tagttgccag ccatctgttg | 540 |
| tttgccccct ccccgtgcct tccttgaccc tggaaggtgc cactcccact gtcctttcct | 600 |
| aataaaatga ggaaattgca tcgcattgtc tgagtaggtg tcattctatt ctgggggtg | 660 |
| gggtggggca ggacagcaag ggggaggatt ggaagacaa tagcaggcat gctgggatg | 720 |
| cggtgggctc tatgggaagt tcctattctc tagaaagtat aggaacttca cgtcggcagt | 780 |
| gaaaaaatg ctttatttgt gaaatttgtg atgctattgc tttatttgta accattataa | 840 |
| gctgcaataa acaagttaac aacaacaatt gcattcattt tatgtttcag gttcaggggg | 900 |
| aggtgtggga ggttttttaa agcaagtaaa acctctacaa atgtggtatg ctgattatg | 960 |
| atcctctaga catatgttag aaggggtgga tgtatacgcg gtccctcttt cttcgggcag | 1020 |
| gcttggccac tcatggtcg ccgccggccc ccttgatctt gtccacctgg ccctggatct | 1080 |
| tgctggcaaa ggtcgcacag cgttgcggca gccacttctt gagcaggtca gaacactgca | 1140 |
| cgttggcaag cccttttgagg cagccagttt gcagtccac acacagatcg acctgtgcga | 1200 |
| tgaactgctc catgggctcc aagtccttga acccaggaat ctcaggaatg tcgacgatcg | 1260 |
| cctcgcctat gccgcctgt gcggactctt tgtcgccttc gtaggtgtgg cagcgtcctg | 1320 |
| ggatgaactt cttcatcttg ggcgtgcact tgatgtggga caggcagatc agacagcccc | 1380 |
| tggtgcagcc agcttccgg gcattggctt ccatctcttt gagcacctcc agcggcagct | 1440 |
| tcttgccggg caacttcccg cggtcagcat cgagatccgt ggtcgcgaag ttgctggcca | 1500 |
| cggccacgat gttgaagtct tcgttgttct cggtgggctt ggcctcggcc acagcgatgc | 1560 |
| agatcagggc aaacagaact ttgactccca tggtgtttac gagggtagga agtggtacgg | 1620 |
| aaagttggta taagacaaaa gtgttgtgga attgaagttt actcaaaaaa tcagcactct | 1680 |
| tttataggcg ccctggttta cataagcaaa gcttatacgt tctctatcac tgataggag | 1740 |
| taaactggat atacgttctc tatcactgat agggagtaaa ctgtagatac gttctctatc | 1800 |
| actgataggg agtaaactgg tcatacgttc tctatcactg atagggagta aactccttat | 1860 |
| acgttctcta tcactgatag ggagtaaagt ctgcatacgt tctctatcac tgataggag | 1920 |
| taaactcttc atacgttctc tatcactgat agggagtaaa ctcgagagag aaatgttctg | 1980 |
| gcacctgcac ttgcactggg gacagccat tttgctagtt tgttttgttt cgttttgttt | 2040 |
| tgatggagag cgtatgttag tactatcgat tcacacaaaa aaccaacaca cagatgtaat | 2100 |

```
gaaaataaag atattttatt ctcgaggtga taattccacg gggttggggt tgcgcctttt    2160
ccaaggcagc cctgggtttg cgcagggacg cggctgctct gggcgtggtt ccgggaaacg    2220
cagcggcgcc gaccctgggt ctcgcacatt cttcacgtcc gttcgcagcg tcacccggat    2280
cttcgccgct acccttgtgg gccccccggc gacgcttcct gctccgcccc taagtcggga    2340
aggttccttg cggttcgcgg cgtgccggac gtgacaaacg gaagccgcac gtctcactag    2400
taccctcgca gacggacagc gccagggagc aatggcagcg cgccgaccgc gatgggctgt    2460
ggccaatagc ggctgctcag cagggcgcgc cgagagcagc ggccgggaag gggcggtgcg    2520
ggaggcgggg tgtggggcgg tagtgtgggc cctgttcctg cccgcgcggt gttccgcatt    2580
ctgcaagcct ccggagcgca cgtcggcagt cggctccctc gttgaccgaa tcaccgacct    2640
ctctccccag ggggatcatc gaattaccat gtctagactg gacaagagca aagtcataaa    2700
ctctgctctg gaattactca atggagtcgg tatcgaaggc ctgacgacaa ggaaactcgc    2760
tcaaaagctg ggagttgagc agcctaccct gtactggcac gtgaagaaca gcgggccct    2820 gctcgatgcc ctgccaatcg agatgctgga caggcatcat acccactcct gccccctgga    2880
aggcgagtca tggcaagact ttctgcggaa caacgccaag tcataccgct gtgctctcct    2940
ctcacatcgc gacggggcta aagtgcatct cggcaccccgc caacagaga aacagtacga    3000 aaccctggaa aatcagctcg cgttcctgtg tcagcaaggc ttctcccctgg agaacgcact    3060 gtacgctctg tccgccgtgg gccactttac actgggctgc gtattggagg aacaggagca    3120
tcaagtagca aagaggaaa gagagacacc taccaccgat tctatgcccc cacttctgaa    3180
acaagcaatt gagctgttcg accggcaggg agccgaacct gccttccttt tcggcctgga    3240
actaatcata tgtggcctgg agaaacagct aaagtgcgaa agcggcgggc cgaccgacgc    3300
ccttgacgat tttgacttag acatgctccc agccgatgcc cttgacgact ttgaccttga    3360
tatgctgcct gctgacgctc ttgacgattt tgaccttgac atgctccccg ggtaa         3415
```

<210> SEQ ID NO 9
<211> LENGTH: 116
<212> TYPE: PRT
<213> ORGANISM: Artificial Sequence
<220> FEATURE:
<223> OTHER INFORMATION: PDZK1 protein repressor

<400> SEQUENCE: 9

```
Met Ala Ser Thr Phe Asn Pro Arg Glu Cys Lys Leu Ser Lys Gln Glu
1               5                   10                  15

Gly Gln Asn Tyr Gly Phe Phe Leu Arg Ile Glu Lys Asp Thr Asp Gly
            20                  25                  30

His Leu Ile Arg Val Ile Glu Glu Gly Ser Pro Ala Glu Lys Ala Gly
        35                  40                  45

Leu Leu Asp Gly Asp Arg Val Leu Arg Ile Asn Gly Val Phe Val Asp
    50                  55                  60

Lys Glu Glu His Ala Gln Val Val Glu Leu Val Arg Lys Ser Gly Asn
65                  70                  75                  80

Ser Val Thr Leu Leu Val Leu Asp Gly Asp Ser Tyr Glu Lys Ala Val
                85                  90                  95

Lys Asn Gln Val Asp Leu Lys Glu Leu Asp Gln Ser Gln Arg Glu Ala
            100                 105                 110

Ala Leu Asn Asp
        115
```

```
<210> SEQ ID NO 10
<211> LENGTH: 8
<212> TYPE: PRT
<213> ORGANISM: Artificial Sequence
<220> FEATURE:
<223> OTHER INFORMATION: angiotensin II

<400> SEQUENCE: 10

Glu Gly Val Asp Val Tyr Ala Val
1               5

<210> SEQ ID NO 11
<211> LENGTH: 23
<212> TYPE: DNA
<213> ORGANISM: Artificial Sequence
<220> FEATURE:
<223> OTHER INFORMATION: CDS

<400> SEQUENCE: 11
gaaaccagtc cgggttactt ggg                                           23

<210> SEQ ID NO 12
<211> LENGTH: 23
<212> TYPE: DNA
<213> ORGANISM: Artificial Sequence
<220> FEATURE:
<223> OTHER INFORMATION: CDS

<400> SEQUENCE: 12
gacccagcaa atacgcctgc agg                                           23

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
ggaaggagta cgggactgtc g                                             21

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
agaggagcag aaaaagcggc                                               20

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
atcatcattc agagcggcct cc                                            22
```

GENETICALLY ENGINEERED NON-HUMAN MAMMAL, CONSTRUCTION METHOD THEREFOR AND USE THEREOF

The present application claims the priority of the Chinese Patent Application No. 201710292460.X, entitled "Genetically Engineered Non-Human Mammal, and the Construction Method therefor and Use thereof", filed on Apr. 28, 2017; and International Patent Application No. PCT/CN2018/085097, entitled "Genetically Engineered Non-Human Mammal, and the Construction Method therefor and Use thereof", filed on Apr. 28, 2018; which are incorporated herein by reference in their entirety.

FIELD

The present invention relates to genetically engineered non-human mammal and cells, organs and tissues; to use thereof in medicinal and disease research; to a method for producing non-human animals and cells, organs and tissues; and to a method for researching in medicine and disease by virtue of the non-human mammals or cells, organs or tissues.

BACKGROUND

Atherosclerosis (AS) and cardiovascular death resulted therefrom, such as myocardial infarction and stroke, are the first reasons causing human death of disease. AS is a vascular disease caused by multiple factors, with lipid metabolism disorders, i.e. hyperlipidemia and hypertension, being major pathogenic risk-factors. The existing construction strategies for AS animal model are based on high fat induction. Specifically, it is usually necessary to add a high-fat diet to induce AS based on the metabolism of key genes of genetically inactivated lipid. Single knockout animal models, for example, apolipoprotein E (ApoE) knockout mice [1], in the case of administrating normal diet, have blood lipids in juvenile or adolescents that are comparable to wild-type mice of the same age. Another example is the scavenger receptor class B type I (SR-BI) knockout mice [2], as mice with a liver-selective cholesterol-uptaking disorder. Although the SR-BI knockout mice have metabolic defects in high-density lipoprotein cholesterol (HDL-C), their metabolism for low-density lipoprotein cholesterol (LDL-C) is not affected. Moreover, the mice have developmentally abnormal embryo [3]. Therefore, the experimental data as collected according thereto are not accurate and thus cannot be used for research. Double knockout animal models, for example, ApoE/PDZK1 double knockout mice [4], are mice with ApoE universal knockout and SR-BI protein 95% down-regulation in the liver; they, as compared with ApoE knockout mice, have unchanged LDL-C and HDL-C. Another example is highly lethal mice that are ApoE/SR-BI double knockout [5], the mice, at 5 weeks after birth on normal diet, suffer from severe atherosclerosis, cardiac hypertrophy, heart failure, and heart dysfunction, and all mice died at 8 weeks old.

But beyond those, at present, there is no simple and effective AS model for the co-action of hyperlipidemia and hypertension. The current ApoE knockout+hypertension animal model are mainly based the following construction strategies. One is the administration of angiotensin II (Ang II) to ApoE knockout mice [6], specifically by osmotic pump implanted in mice. This strategy is complicated, would trigger inflammation to mice from trauma, and is not convenient for administration regulation. The other is produced by applying clip operation on the kidneys of ApoE knockout mice to stimulate renin, so as to trigger hypertension [7]. This strategy model is difficult to construct, and would produce relatively insignificant hyperlipidemia and atherosclerosis effects. Another is a model of hypercholesterolemia and hypertension (HC/HT) [8], this model is obtained by cross-breeding ApoE knockout mice with and mice that carry human renin genes and angiotensin (REN+AGT+) Transgenic. Mice are born with defects of hypertension and lipid metabolism, with hypertension being uncontrollable.

There is still a need for effective animal models of hyperlipidemia and/or hypertension in the art.

SUMMARY

According to the first aspect, the present invention provides a genetically engineered non-human mammal, wherein the non-human mammal has a genome with the ApoE gene therein being functionally inactivated, and wherein the genome comprises an exogenous polynucleotides comprising the coding sequence of one or more scavenger receptor class B type I (SR-BI) knockdown factors and/or comprising the coding sequence(s) of one or more vasoconstrictors, the coding sequence(s) of SR-BI knockdown factor being operably linked to a tissue-specific promoter, and the coding sequence(s) of the vasoconstrictors being operably linked to an inducible promoter.

According to the second aspect, the present invention provides cell, organ or tissue of the genetically engineered non-human mammal, wherein the non-human mammal has a genome with the ApoE gene therein being functionally inactivated, and wherein the genome comprises an exogenous polynucleotides comprising the coding sequence of one or more SR-BI knockdown factors and/or comprising the coding sequence(s) of one or more vasoconstrictors, the coding sequence(s) of SR-BI knockdown factor being operably linked to a tissue-specific promoter, and the coding sequence(s) of the vasoconstrictors being operably linked to an inducible promoter.

According to the third aspect, the present invention provides a method of producing a genetically engineered non-human mammal, comprising: functionally inactivating ApoE genes in genomes of animal embryonic stem cells or fertilized egg or germ cell; and integrating an exogenous polynucleotide into the genome of the animal embryonic stem cell or fertilized egg, wherein the exogenous polynucleotide comprises the coding sequence of one or more SR-BI knockdown factors and/or the coding sequence(s) of one or more vasoconstrictors, and wherein the coding sequence of the SR-BI knockdown factor is operably linked to a tissue-specific promoter, and the coding sequence of vasoconstrictor is operably linked to an inducible promoter.

The invention also relates to an isolated non-human mammalian cell, tissue or organ, which derives from the genetically engineered non-human mammal produced by the method according to the third aspect.

The present invention further relates to a method of screening or verifying drug, comprising providing a candidate drug, administering the candidate drug to the genetically engineered non-human mammal according to the first aspect or the animal produced by the method according to the third aspect, or contacting the candidate drug with the cell, tissue, or organ according to the second aspect, and verifying whether the animal or the cell, tissue, or organ produces a desired response to the drug.

BRIEF DESCRIPTION OF THE DRAWINGS

FIG. 5 is a graph showing the effect of the lipid metabolism defect on the heart studied by using the mice according to the present invention. A to D show the results of four blood lipid tests in mice; E is the ratio of heart weight to body weight of mice; F is the body weight of mice; G is the inner diameter of left ventricular of the mice at systolic phase; H is the inner diameter of left ventricular of the mice at diastolic phase; I is the ejection fraction; J is the fractional shortening; K is the heart picture of mice; L is the observed image under microscope of mice heart slice with oil red O stained (bar=800 μm) and partial enlargement thereof (bar=50 μm). $P<0.01$, *$P<0.001$. Wt refers to wild-type mice, Het is heterozygous mice, Hom refers to homozygous mice, and KO refers to ApoE knockout mice having traditional lipid metabolism defects.

DETAILED DESCRIPTION

Figure 1:
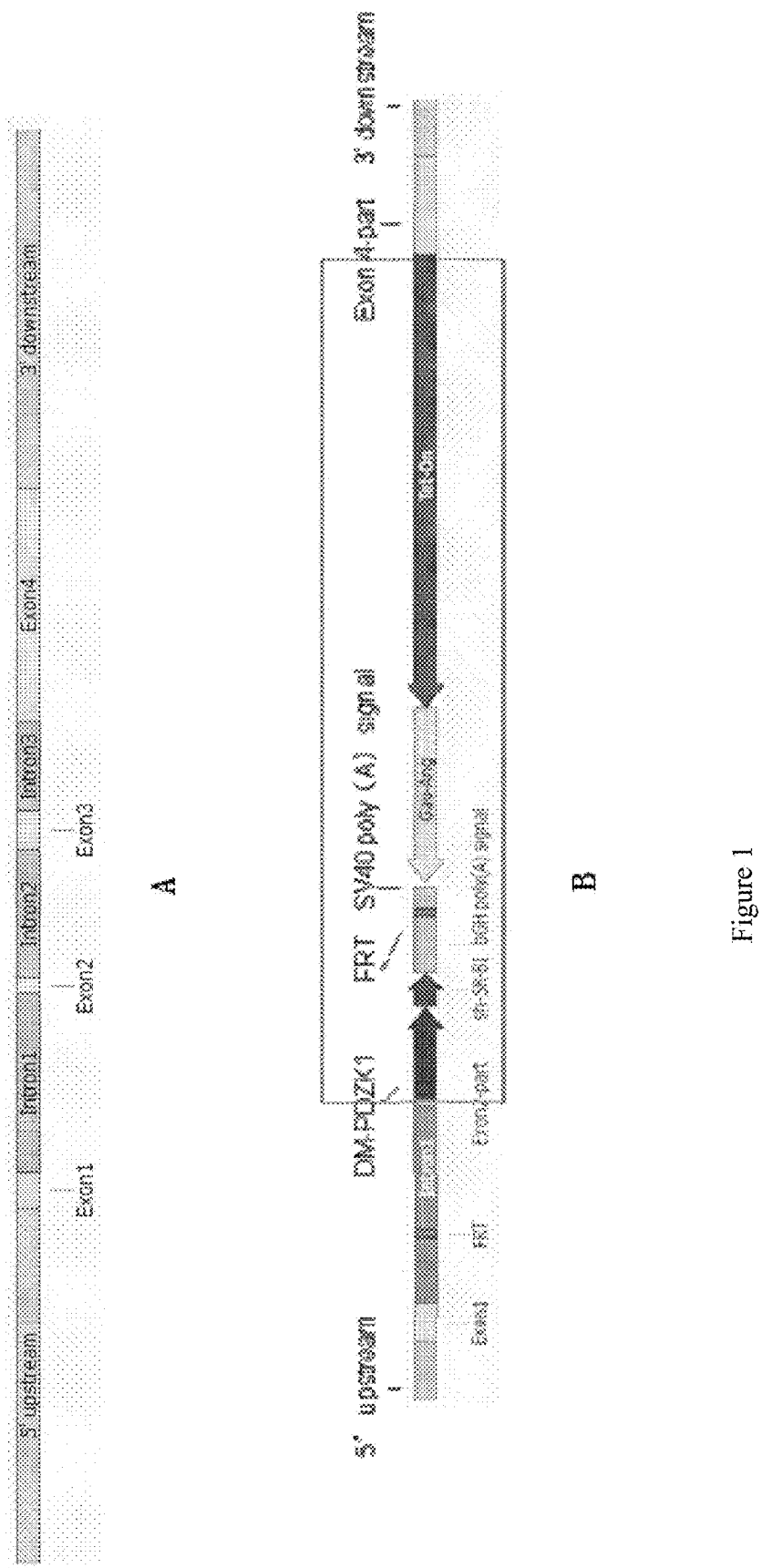
FIG. 1 shows the insertion of a constructed X sequence into a wild-type ApoE gene. A is a schematic diagram of the wild-type ApoE gene of the mice; B is a schematic diagram of the gene at the ApoE locus of the constructed transgenic mice.

According to one aspect of the present invention, this is provided a genetically engineered non-human mammal, wherein the non-human mammal has an genome with the ApoE gene therein being functionally inactivated, and wherein the genome comprises an exogenous polynucleotides comprising the coding sequence of one or more scavenger receptor class B type I (SR-BI) knockdown factors and/or comprising the coding sequence(s) of one or more vasoconstrictors, the coding sequence(s) of SR-BI knockdown factor being operably linked to a tissue-specific promoter, and the coding sequence(s) of the vasoconstrictors being operably linked to an inducible promoter.

"Genetically engineered" animal, cell, tissue or organ means an animal, cell, tissue or organ comprising an exogenous polynucleotide or modified gene sequence or expression regulatory sequence in the genome thereof. For example, the exogenous polynucleotide could be stably integrated into the genome of the animal, cell, tissue or organ, and inherit a continuous generation. The exogenous polynucleotide may be integrated into the genome alone or as part of a recombinant DNA construct. The modified gene sequence or expression regulatory sequence means that the sequence, in the genome of an animal, cell, tissue or organ, comprises substitutions, deletions and additions of single or multiple deoxynucleotide.

As used herein, "non-human mammals" include, but are not limited to, experimental animals or other animals, such as rabbits, rodents (for example, mice, rats, hamsters, gerbils and guinea pigs), cattles, sheep, pigs, goats, horses, dogs, cats, primates (such as chimpanzees, rhesus monkeys and cynomolgus monkeys). Preferred animals include Chinese hamsters, rats, mice, dogs, pigs, rabbits, and monkeys.

"Exogenous" with respect to a sequence means a sequence from an alien species, alternatively, from the same species with the proviso that the sequence is changed from its native significantly in composition and/or locus by virtue of deliberate human intervention.

"Polynucleotide", "nucleic acid sequence", "nucleotide sequence", or "nucleic acid fragment", as used interchangeably, are single- or double-stranded RNA or DNA polymers, optionally containing synthetic, non-natural or changed nucleotide bases. Nucleotides are represented by means of single letter designation thereof: "A" represents adenosine or deoxyadenosine (corresponding to RNA or DNA respectively), "C" represents cytidine or deoxycytidine, "G" represents guanosine or deoxyguanosine, "U" represents uridine, "T" represents deoxythymidine, "R" represents purine (A or G), "Y" represents pyrimidine (C or T), "K" represents G or T, "H" represents A or C or T, "I" represents inosine, and "N" represents any nucleotide.

As used herein, the term "operably linked" refers to functionally effective linkage between regulatory elements (such as, but not limited to, a promoter sequence, a transcription termination sequence) and target nucleic acid sequence (for example a coding sequence or an open reading frame), so that the transcript of nucleic acid sequence is controlled and regulated by the regulatory elements for transcript. Techniques of rendering regulatory element regions operably linked to nucleic acid molecules are known in the art.

As used herein, "functionally inactivated/functionally inactivating" includes, but is not limited to, inactivated mutations of the genes themselves, and inactivated mutations of elements that regulate gene expression. Mutation may be substitutions, additions and deletions of single or multiple base. For example, the mutation can be achieved by a gene editing tool such as CRISPR system.

Examples of functionally inactivating include, but are not limited to, deletions or partial deletions, frameshift mutations, and cleavage site mutations of gene or gene promoter. Functionally inactivating may also be achieved by inserting an exogenous polynucleotide into the gene to be inactivated, or by replacing part or all of the sequence of the gene to be inactivated with an exogenous polynucleotide.

"Promoter" refers to a nucleic acid fragment that is capable of controlling the transcription of another nucleic acid fragment. In some embodiments according to the present invention, a promoter is a promoter capable of controlling the transcription of gene in a cell, whether it is derived from the cell or not.

As used herein, "tissue-specific promoter" is a promoter that renders a gene to express substantially in some specific organs or tissue sites, such as the liver. In some embodiments, the "tissue-specific promoter" is an ApoE gene promoter, such as an endogenous ApoE gene promoter. In some embodiments, the expression of the coding sequence of SR-BI knockdown factor is driven by endogenous ApoE gene promoter. By using the ApoE promoter, specific knockdown of the SR-BI protein in tissues and organs such as the liver may be achieved.

As used herein, "SR-BI knockdown factor" refers to a factor that is capable of reducing the level of SR-BI having activity in an animal in protein level and/or transcription level, for example, the factor reduces the level of SR-BI having activity by transcription-level control, post-transcription-level control, translation-level control, and post-translation-level control. For example, the SR-BI knockdown factor may be a repressor protein that directly or indirectly reduces the activity of the SR-BI protein, an antibody for the SR-BI protein, an siRNA for SR-BI transcript, and an antisense RNA. For example, the factor that reduces the level of SR-BI having activity is the repressor of PDZK1 protein. As is known in the art, PDZK1 protein is an adaptor protein containing four PDZ domains, it may bind to the intracellular carboxy terminus of SR-BI, thereby regulating the stability and activity, and localization and function of SR-BI. PDZK1 knockdown may result in the down-regulation of SR-BI expression in liver and small intestine respectively by 95% and 50%, but result in a little or substantially no down-regulation of SR-BI expression in other tissues. In the present invention, a repressor protein is used to inhibit the activity of PDZK1, thereby down-regulating the level of SR-BI protein. In some embodiments, the repressor protein that inhibits PDZK1 activity has an amino acid sequence of MASTFNPRECKLSKQEGQNYGFFLRIEKDTDGHLIR-VIEEGSPAEKAGLLDGDRVLRIN GVFVDKEEHAQV-VELVRKSGNSVTLLVLDGDSYEKAVKNQVDLKE-LDQSQREAALN D, as shown in SEQ ID NO.9.

In some embodiments, the coding sequence flanking of the SR-BI knockdown factor comprises the element of recombinase system. In some embodiments, the recombinase system is a FLP/FRT recombinase system, and the element is a FRT sequence. In the present invention, an animal whose genome has coding sequence of the SR-BI knockdown factor and coding sequence of the vasoconstrictor could propagate with the animal whose genome has FLP recombinase gene sequence, obtaining animal whose genome only have coding sequence of the vasoconstrictor.

In some embodiments, the coding sequences of the siRNA corresponding to SR-BI transcript have homogenies of 56%, 60%, 65%, 70%, 75%, 80%, 85%, 90%, 95%, 99% to the sequence as shown in SEQ ID NO. 4. SEQ ID NO. 4 has a sequence of 5'-CCTGGAGGCTTGCT-GAAGGCTGTATGCTG AATAATCGATCTTGCTGAGT-CGTTTTG GCCACTGACTGACGACTCAGCGATCGAT-TATT CAGGACACAAGGCCTGTTACTAGCACTCA-CATGGAACAAATGGCCC-3'. The underlined sequence portion of SEQ ID NO. 4 can be substituted by other interference sequences for SR-BI transcript. In some particular embodiments, siRNA is sh-m-SR-BI, with a coding sequence as shown in SEQ ID NO. 4.

In some embodiments, the vasoconstrictor is angiotensin II. In some embodiments, the angiotensin II has an amino acid sequence of EGVDVYAV. In some embodiments, the angiotensin II carries a detectable tag. The amount of the detectable tag can be used to reflect the expression amount of the angiotensin II. For example, the detectable tag may be selected from luciferase, such as Gauss luciferase, firefly luciferase, and sea cucumber luciferase; and fluorescent proteins. In some particular embodiments, the detectable tag is Gauss luciferase. In some embodiments, the detectable tag is linked to the vasoconstrictor by a linker cleavable in vivo.

As used herein, an "inducible promoter" selectively expresses an operably linked DNA sequence in response to an endogenous or exogenous stimulus (environment, hormone, chemical signal, etc.). In some embodiments, the inducible promoter is a chemical inducible promoter. In some particular embodiments, the chemical inducible promoter is a tetracycline-inducible promoter.

According to another aspect of the present invention, this is provided cell, organ or tissue derived from the genetically engineered non-human mammal, wherein the non-human mammal has a genome with the ApoE gene therein being functionally inactivated, and wherein the genome comprises an exogenous polynucleotides comprising the coding sequence of one or more SR-BI knockdown factors and/or comprising the coding sequence(s) of one or more vasoconstrictors, the coding sequence(s) of SR-BI knockdown factor being operably linked to a tissue-specific promoter, and the coding sequence(s) of the vasoconstrictors being operably linked to an inducible promoter.

In some embodiments, the cell is one that is unable to develop into a complete biomass, such as a somatic cell, a hepatocyte.

In some embodiments, functionally inactivating may be achieved by inserting an exogenous polynucleotide into the ApoE gene, or by replacing part or all of the sequence of the ApoE gene with an exogenous polynucleotide. In some embodiments, the exogenous polynucleotide is integrated into the locus of the ApoE gene.

In some embodiments, the tissue-specific promoter is an ApoE gene promoter, such as an endogenous ApoE gene promoter. In some embodiments, the expression of the coding sequence of the SR-BI knockdown factor is driven by an endogenous ApoE gene promoter.

In some embodiments, the coding sequence flanking of the SR-BI knockdown factor comprises element of recombinase system. In some embodiments, the recombinase system may be a FLP/FRT recombinase system, and the element of recombinase system may be a FRT sequence. The element of recombinase system can be used to remove the coding sequence of the SR-BI knockdown factor by crossing with the animal expressing FLP.

In some embodiments, the coding sequences of the siRNA corresponding to SR-BI transcript have homogenies of 56%, 60%, 65%, 70%, 75%, 80%, 85%, 90%, 95%, 99% to the sequence as shown in SEQ ID NO.4. In some particular embodiments, siRNA has the coding sequence of sh-m-SR-BI, the sequence of which is shown in SEQ ID NO.4.

In some embodiments, the vasoconstrictor is angiotensin II. In some embodiments, angiotensin II has an amino acid sequence of EGVDVYAV. In some embodiments, the angiotensin II carries a detectable tag. For example, the detectable tag may be selected from luciferase, such as Gauss luciferase, firefly luciferase, and sea cucumber luciferase; and fluorescent proteins. In some particular embodiments, the detectable tag is Gauss luciferase.

In some embodiments, the inducible promoter is a chemical inducible promoter. In some embodiments, the chemical inducible promoter is a tetracycline-inducible promoter.

According to still another aspect of the invention, this is provided a method of producing a genetically engineered non-human mammal, comprising: functionally inactivating ApoE genes in genomes of animal embryonic stem cells or fertilized egg or germ cell; and integrating an exogenous polynucleotide into the genome of the animal embryonic stem cell or fertilized egg, wherein the exogenous polynucleotide comprises the coding sequence of one or more SR-BI knockdown factors and/or the coding sequence(s) of one or more vasoconstrictors, and wherein the coding sequence of the SR-BI knockdown factor is operably linked to a tissue-specific promoter, and the coding sequence of vasoconstrictor is operably linked to an inducible promoter.

In some embodiments, functionally inactivating may be achieved by inserting an exogenous polynucleotide into the ApoE gene, or by replacing part or all of the sequence of the ApoE gene with an exogenous polynucleotide.

In some embodiments, the tissue-specific promoter is an ApoE gene promoter.

The present invention may achieve tissue-specific expression of the coding sequence of the SR-BI knockdown factor by using endogenous ApoE gene promoter. Thus, the present invention also provides a method of producing a genetically engineered non-human mammal, comprising: functionally inactivating ApoE genes in genomes of animal embryonic stem cells or fertilized egg or germ cell; and integrating an exogenous polynucleotide into the genome of the animal embryonic stem cell or fertilized egg, wherein the exogenous polynucleotide comprises the coding sequence of one or more SR-BI knockdown factors and/or the coding sequence(s) of one or more vasoconstrictors, and wherein the coding sequence of vasoconstrictor is operably linked to an inducible promoter, and the exogenous polynucleotide is integrated at the downstream of the promoter of the ApoE gene in the genome, such that the SR-BI knockdown factor is operably linked to a promoter of ApoE gene.

In some embodiments, the exogenous polynucleotide is integrated into the locus of the ApoE gene. In some embodiments, the integration is achieved by homologous recombination. In some embodiments, the homologous recombination is achieved by a CRISPR/Cas9 system-mediated site-directed homologous recombination. The homologous recombination may be achieved, for example, by introducing the CRISPR/Cas9 system and targeting vector into cell, wherein the CRISPR/Cas9 system targets to the specific site within the ApoE gene, and the targeting vector carries the exogenous polynucleotide with flanking being ApoE homologous sequence.

In some embodiments, the coding sequence of the SR-BI knockdown factor has a flanking comprising element of recombinase system. In some particular embodiments, the recombinase system is a FLP/FRT recombinase system.

In some embodiments, the coding sequences of the siRNA corresponding to SR-BI transcript have homogenies of 56%, 60%, 65%, 70%, 75%, 80%, 85%, 90%, 95%, 99% to the sequence as shown in SEQ ID NO.4. In some particular embodiments, the siRNA is encoded as sh-m-SR-BI, the sequence of which shown in SEQ ID NO. 4.

In some embodiments, the vasoconstrictor is angiotensin II. In some particular embodiments, angiotensin II has an amino acid sequence of EGVDVYAV, as shown in SEQ ID NO.10. In some embodiments, the angiotensin II carries a detectable tag. For example, the detectable tag may be selected from luciferase, firefly luciferase, sea cucumber luciferase, and fluorescent protein. In some particular embodiments, the detectable tag is Gauss luciferase.

In some embodiments, the inducible promoter is a chemical inducible promoter. In some embodiments, the chemical inducible promoter is a tetracycline-inducible promoter.

According to still another aspect of the invention, this is provided a method of producing cell, tissue or organ of a non-human mammal, comprising isolating cell, tissue or organ cell from the genetically engineered non-human mammal according to the present invention or from the genetically engineered non-human mammal produced by the method according to the present invention.

According to still yet another aspect of the invention, this is provided a method of screening or verifying a drug, comprising providing a candidate drug, administering the candidate drug to the genetically engineered non-human mammal according to the present invention or the animal produced by the method according to the present invention, or contacting the candidate drug with the cell, tissue, or organ of the genetically engineered non-human mammal according to the present invention, and verifying whether the cell, tissue, or organ produces a desired response to the drug.

In various aspects of the invention, the animal may mimic a pathological condition or disorder selected from hyperlipemia, hypertension, or a disease of heart, brain, blood vessels and kidney related to hyperlipidemia and/or hypertension. For example, the animal may mimic a disease including, but not limited thereto, one or more of atherosclerosis, vascular remodeling disease, aneurysm, myocardial infarction, thrombotic disease, heart failure, cardiac hypertrophy, renal function abnormity, aortic anomalous, lipid metabolic disorder, fatty liver, fundus vascular disease, coronary heart disease, stroke, cardiac hypertrophy, arrhythmia, hyperlipidemia, vascular abnormalities, arteries stenosis, microcirculatory disorder, renal aneurysm, obesity, xanthoma, hearing impairment, drug-resistant epilepsy, eclampsia, cerebral vasospasm, Alzheimer's disease and vascular dementia, blood-brain barrier abnormality, low immunity, olfactory degeneration, pulmonary hypertension, pulmonary embolism, and diabetes. In some embodiments, the animal-mimicked hypertension or hypertension-related pathological condition or disorder may be induced, for example, by a chemical (tetracycline). In some embodiments, the desired response is the prevention or delay of at least one condition selected from a lipid metabolism disorder, liver function abnormity, fatty liver, glucose metabolism disorder, increasing of systolic blood pressure and/or diastolic blood pressure, cardiac function abnormality, myocardial ischemia, atherosclerotic plaque formation, renal function abnormity. In some embodiments, the desired response is the improvement or stabilization of at least one condition selected from a lipid metabolism disorder, liver function abnormity, fatty liver, glucose metabolism disorder, systolic blood pressure and/or diastolic blood pressure, cardiac function, myocardial ischemia, atherosclerotic plaque, renal function abnormity. In some embodiments, the desired response indicates that the drug is useful for treating or preventing the pathological condition or disorder.

The invention also relates to a method of producing a genetically engineered non-human mammal for using as an inducible hypertensive animal model, comprising crossing a first parent animal with a second parent animal, wherein the first parent animal is the genetically engineered non-human mammal according to the present invention or the genetically engineered non-human mammal produced by the method of according to the present invention, and the second parent animal is an animal having a FLP recombinase coding sequence in the genome, and wherein the first parent animal has a coding sequence of SR-BI knockdown factor with the flanking being FRT sequences. Animals produced by this method can avoid hyperlipemia-related effects to some extent.

The scope of the invention is determined by claims as appended. In the context of the claims, the terms "comprise/include/contain" or "comprising/including/containing" does not exclude other possible elements or steps. In addition, the reference to "a/an" or "one" etc. should not be construed as excluding more or multiple. Individual features recited in the different claims may be advantageously combined. Moreover, reciting the features in the different claims does not exclude possible and advantageous combination of these features.

The invention is described in detail below by way of examples. Although many examples of the present invention are described below, the scope of the invention is not limited to the thereto.

EXAMPLES

The mice as used in the examples are available from Beijing Biocytogen Co., Ltd; unless otherwise stated, in the experiments of the examples, the reagents and instruments as employed are commercially available. The normal diets thereof are available from Beijing Huakang Biotechnology Co., Ltd., containing 18% protein, 4% fat, 5% fiber, other trace elements and sterilized water. In the examples, all of the inserted polynucleotide sequences, available from the NCBI database, are artificially synthesized, by synthesis company Genscript Biotechnology Co., Ltd. Unless otherwise stated, all the synthesis methods, testing method etc. as employed in the examples are conventional.

Example 1 Preparation of Exogenous Polynucleotide Sequences

Synthesizing a polynucleotide sequence to be inserted into the mice genome, comprising the following elements (named as an X polynucleotide sequence, as shown in SEQ ID NO. 8):
- a polynucleotide sequence based on 5' upstream end of exon 2 of the mice ApoE gene (with exon 2 locating in the antisense strand of chromosome 7 of mice: 19, 696, 109-19, 699, 188, having NCBI ID as 11816), the 5' end being the start codon of exon 2; the element sequence is shown in SEQ ID NO. 2;
- DM-PDZK1-flag, a polynucleotide sequence of the repressor protein of PDZK1 protein coding with flag tag, wherein the polynucleotide sequence, using a promoter of ApoE gene, reduces the level of SR-BI having activity in organisms at protein level; the element sequence is shown in SEQ ID NO. 3, wherein the sequence 5'-GATTACAAGGATGACGACGATAAG-3' is the flag sequence;
- Sh-m-SR-BI, a polynucleotide sequence with coding comprising siRNA which has a coding corresponding to SR-BI gene, wherein the polynucleotide sequence, using a promoter of ApoE gene, reduces the mRNA content of SR-BI in organisms at transcript level; the element sequence is shown in SEQ ID NO. 4;
- BGH poly (A), a transcription termination sequence;
- FRT, a FRT recombination site polynucleotide sequence; the mice having a FRT recombination site polynucleotide sequence in the genome may be mated with the mice having a FLP recombinase polynucleotide sequence in the genome, which may knock the sequence between two FRT sites;
- SV40 poly (A) signal, a transcription termination sequence;
- Gau-Ang II, a polynucleotide sequence with coding coupling angiotensin II of Gauss luciferase, the angiotensin II and Gauss luciferase are translated into a protein together, and the protein, after being translated, is cleaved, by an endogenous protease, into two independent proteins, Gauss luciferase and angiotensin II; the element sequence is shown in SEQ ID NO. 5;
- Tet-On: a polynucleotide sequence of a promoter element that can be induced by tetracycline, which can be induced by tetracycline or a tetracycline analog doxycycline to initiate expression of the gene at downstream;
- partial sequence of exon 4 based mice ApoE gene; the element sequence is shown in SEQ ID NO. 6.

Example 2 Construction of Targeting Plasmid

The following polynucleotide elements were synthesized:
a polynucleotide sequence based on the 5' end upstream of the mice ApoE gene to intron 1, with a FRT sequence, i.e. a FRT recombination site polynucleotide sequence, being inserted thereto; the element sequence is shown in SEQ ID NO. 1;
X polynucleotide sequence prepared in Example 1;
a downstream sequence of exon 4 based on mice ApoE gene; the element sequence is shown in SEQ ID NO. 7.

Figure 2:
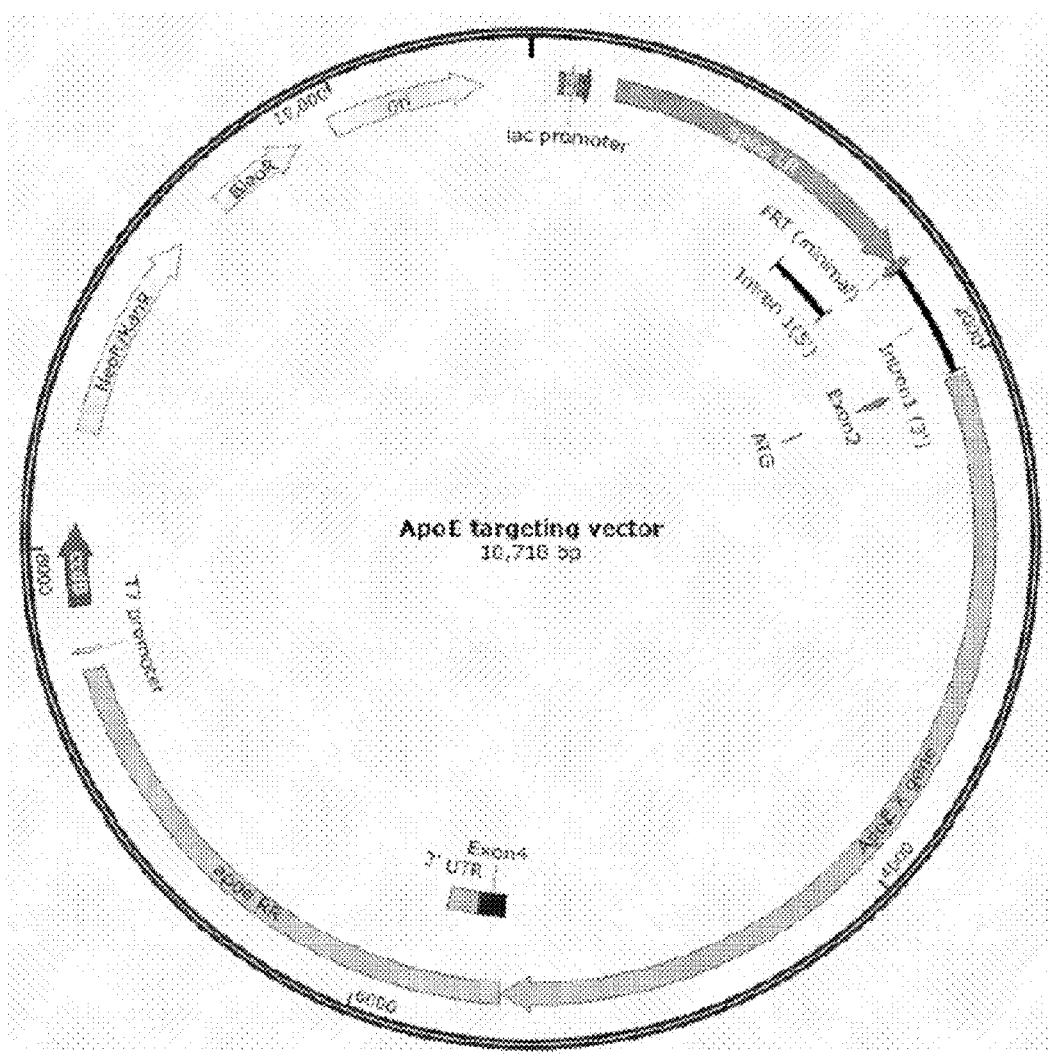
FIG. 2 is a schematic diagram of a target plasmid.

The above sequences are connected in tandem, and are connected into a plasmid vector carrying T7 promoter. The targeting plasmid as constructed is shown in FIG. 2.

Example 3 Construction of Recombinant Mice

The construction steps are as follows:
1. Preparation of sgRNA

According to the design principle of sgRNA known in the art, for the ApoE gene sites, there are designed two polynucleotide sequences encoding sgRNA as follows:

(SEQ ID NO. 11)
5'-GAAACCAGTCCGGGTTACTTGGG-3'

(SEQ ID NO. 12)
5'-GACCCAGCAAATACGCCTGCAGG-3' wherein the sgRNA is directly obtained by artificial synthesis.

2. Preparation of Cas9/RNA

Synthesizing Cas9/RNA artificially: connecting the above sequences sgRNA into a recombinant plasmid vector carrying T7 promoter and the Cas9 expression sequence (Cas9 sequence is shown in SEQ ID NO. 16) for in vitro transcription, thereby obtaining microinjection Cas9/RNA; and plasmid vector is Precut PCS plasmid available from Beijing Biocytogen Co., Ltd.

3. Preparation of Transgenic Mice

Microinjecting the prepared sgRNA and the Cas9 recombinant plasmid or the Cas9/RNA recombinant plasmid, together with the targeting vector prepared in Example 2, into the fertilized egg of mice, transplanting the fertilized egg that are subjected to the microinjecting into the body of pseudopregnant female mice, and feeding the mice with normal feed, obtaining mice of F0 generation.

As shown in FIG. 1A and FIG. 1B, partial sequence of ApoE gene in the mice genome is replaced with the X polynucleotide sequence of Example 1. In this way, a mice with ApoE gene being knockout, SR-BI gene being knocked down in the liver and hypertension inducible is obtained. As shown in FIG. 1B, since angiotensin II expression is controlled by a tetracycline-inducible promoter, the mice can be induced to produce angiotensin II by tetracycline or tetracycline analog, thereby inducing hypertension.

Furthermore, since FRT recombination sites are inserted into the flanking of the exogenous polynucleotide sequence for reducing the level of SR-BI having activity in the body of mice, there are obtained mice that are subjected to ApoE gene knockout and is hypertension inducible, by mating the transgenic mice with the mice having coding of FLP recombinase gene in the genome (B6/JNju-H11<em1Cin(CAG-FLPo)>/Nju, available from the Model Animal Research Institute of Nanjing University).

Example 4 Verifying and Screening Gene Recombinant Mice

Extracting the genome of mice of F0 generation obtained in Example 3 for gene identification, and the designing and synthesizing the following identification primers:

(SEQ ID NO. 13)
F(5'-GGAAGGAGTACGGGACTGTCG-3')

(SEQ ID NO. 14)
R1(5'-AGAGGAGCAGAAAAAGCGGC-3')

-continued (SEQ ID NO. 15)
R2(5'-ATCATCATTCAGAGCGGCCTCC-3')

Figure 3:
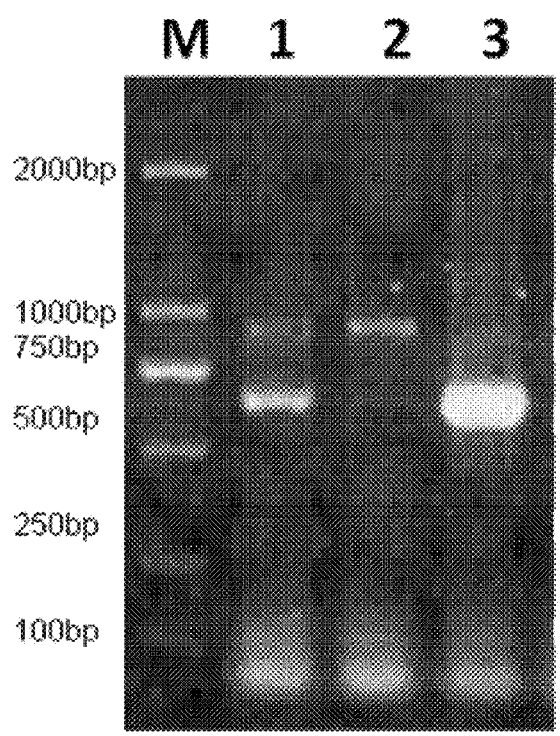
FIG. 3 is the electrophoresis result of agarose, verifying the genotype of transgenic mice. Lane M refers to a marker; lane 1 refers to heterozygous mice; lane 2 refers to homozygous mice; and lane 3 refers to wild-type mice.

Preparing PCR system using synthesized primers, extracted genome of mice of F0 generation, Taq enzyme, dNTP, magnesium ion, and buffer, and performing the PCR under the program of 94° C., 5 min; (94° C., 30 s; 60° C., 30 s; 72° C., 1 min)×35; 22° C., 5 min. Electrophoresing the PCR product using agarose gel: it is identified as wild-type (Wt) in case that there is only one electrophoresis band of about 670 bp, it is identified as homozygous (Hom) in case that there is only one electrophoresis band of about 967 bp, and it is identified as heterozygous (Het) in case that there are electrophoresis bands of about 670 bp and 967 bp at the same time. The identification results are shown in FIG. 3.

F0 generation mice were mated with wild-type mice, to obtain heterozygous F1 generation mice. F1 generation mice were mated with F1 generation mice, and verifying by the above steps to obtain homozygous mice, heterozygous mice, and wild type mice. Homozygous mice and heterozygous mice are ones used in the following experiments. The homozygous mouse, heterozygous mouse used in the examples of the present invention can be continuously obtained by repeating the above passage steps using the progeny mice of F1 mice.

Example 5 Transcript Levels of ApoE, SR-BI Genes in Transgenic Mice

PCR is used to detect the transcript levels of ApoE and SR-BI genes in different organs and tissues of wild-type, homozygous and heterozygous transgenic mice.

Figure 4:
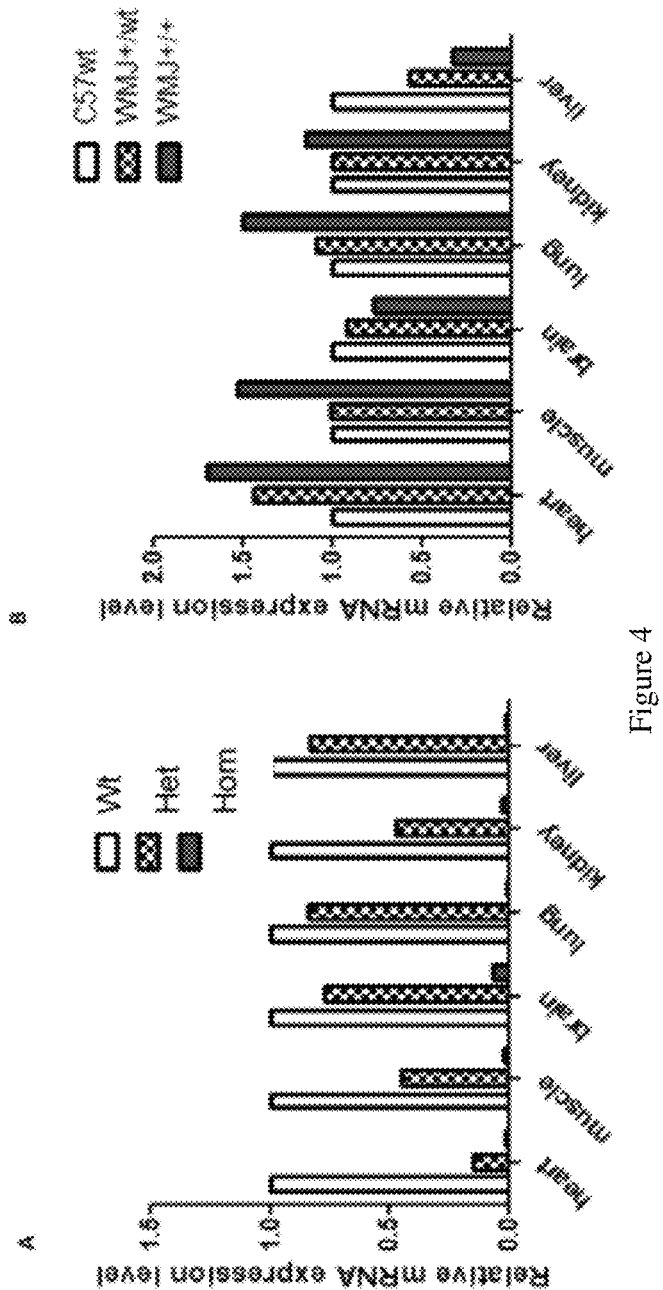
FIG. 4 shows the mRNA transcription of the ApoE gene and the SR-BI gene in different tissues identified by RT-PCR. Wt is wild-type mice, Het refers to heterozygous mice, and Hom refers to a homozygous mice. A: ApoE mRNA expression level; B: SR-BI mRNA expression level.
Figure 6:
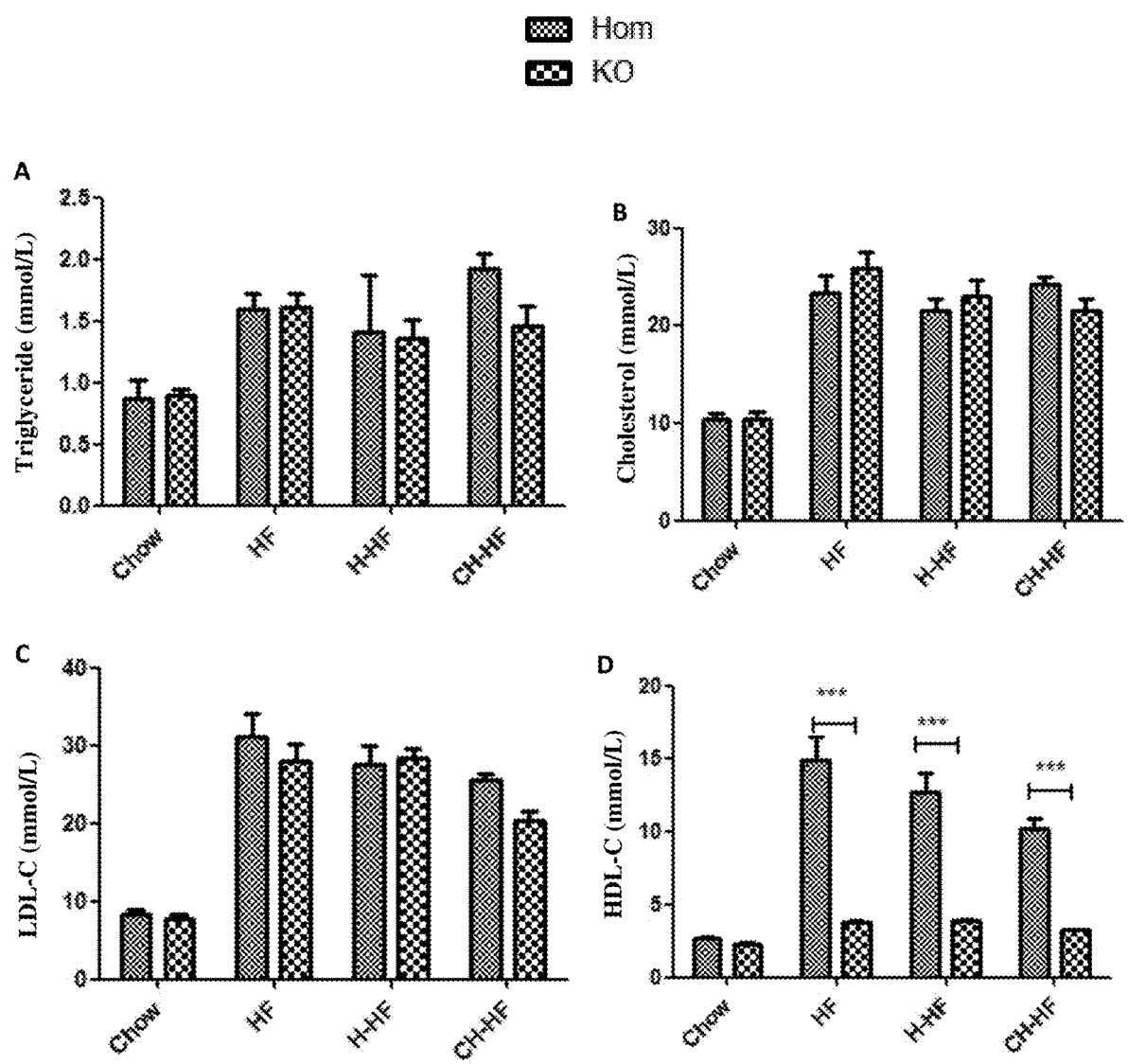
FIG. 6 is a graph showing the effect of hyperlipidemia on atherosclerotic lesions studied by using the mice according to the present invention. A to D show the results of four blood lipid tests in mice. Chow refers to a normal diet group; HF, H-HF, and CH-HF refer to different high-fat diet groups respectively; Hom refers to homozygous mice; and KO refers to ApoE knockout mice. ***$P<0.001$.

The results are shown in FIG. 4A. It can be seen the complete deletion of ApoE expression in all tissues and organs of homozygous mice, and the partial deletion in all tissues and organs of heterozygous mice. The ApoE gene is normally expressed in the corresponding wild-type mice. Furthermore, since the exogenous polynucleotide sequence for reducing the level of active SR-BI in the mice is controlled by the ApoE gene promoter, the expression of gene having coding SR-BI is down-regulated in some tissues or cells of homozygous and heterozygous and mice that are selected in Example 4, as shown in FIG. 4B, the SR-BI gene expression is down-regulated in the livers of homozygous and heterozygous mice.

ApoE gene are completely or partially deleted in the homozygous and heterozygous mice, and the SR-BI protein is down-regulated in some tissues, thus, homozygous and heterozygous mice both have lipid metabolism defect and reverse cholesterol transport (RCT) defects. Therefore, as the mice are fed with normal diet, the homozygous and heterozygous mice will suffer from dyslipidemia and related diseases. High-fat diet would cause early dyslipidemia and related diseases to the homozygous and heterozygous mice.

Example 6 the Study of the Effects of Lipid Metabolism Defects on Heart Using the Mice According to the Present Invention The experiment is employed by dividing the mice into four groups: homozygous (Hom) mice group, heterozygous (Het) mice group, wild-type (Wt) mice group, and ApoE knockout (KO) mice group. Fifteen mice for each group were fed with normal diet until the mice is 3 weeks old. Feeding the mice with a high-fat diet HF (HF formula: 21.2% fat, 48.7% carbohydrate, 17.3% protein, and 0.25% cholesterol) until the mice were 5 weeks old, and examining the body weight, heart weight and blood lipids of the mice.

As shown in FIGS. 5A to 5D, homozygous (Hom) mice, as compared with wild-type (Wt) mice, have high contents of cholesterol (CHOL), low-density lipoprotein cholesterol (LDL-C), and high density lipoprotein cholesterol (HDL-C) in blood. The contents of low-density lipoprotein cholesterol and cholesterol in the blood of homozygous mice have high level similar to those of traditional lipid-deficient mice, ApoE knockout mice (KO), whereas high-density lipoprotein cholesterol in the blood of homozygous mice is higher than that of ApoE knockout mice (KO), which is one of the differences between homozygous mice and traditional lipid metabolism-deficient mice models. In addition, as shown in FIG. 5E to FIG. 5F, the ratio of heart weight to body weight of the homozygous mice is higher than that of the ApoE knockout mouse, indicating that homozygous mice, after being fed with the high fat diet HF for 5 weeks, have the heart being larger, that is, high fat diet induces hyperlipidemia and alters heart development in mice having lipid metabolism defects.

Feeding the mice with high-fat diet (HF) at 8 weeks old until 16 weeks old, and subjecting an ultrasonic testing to the heart of mice at 24 weeks old. As shown in FIGS. 5G and 5H, the left ventricular (LV) inner diameter (ID) of Hom mice increases significantly in systole (s) and diastole (d), as compared with KO mice. As shown in FIGS. 5I and 5J, both the ejection fraction (EF) and the fractional shortening (FS) decreased significantly. This indicates that long-term of high-fat diets make homozygous mice more susceptible to cardiac dysfunction than ApoE knockout mice. Further, as shown in FIG. 5K, the inventors has observed that the heart of homozygous mice is much larger than that of ApoE knockout mice after feeding with long-term of high-fat diet. The heart, after being subjected to OCT embedding, is frozen sectioned, and then frozen sections are stained with Oil Red O. The inventors have found that, as shown in FIG. 5L, the coronary branch of the heart of homozygous mice is more likely to have atherosclerotic plaques, as compared with ApoE knockout mice.

Example 7 Study of Effect of Hyperlipidemia on Atherosclerotic Lesions Using the Mice According to the Present Invention Homozygous mice (Hom) and ApoE knockout mice (KO) are used as controls, the experiment is employed by dividing the mice into four groups, each group has 15 mice, four groups being normal diet group (Chow), high fat diet group (HF), higher fat diet group (H-HF) and ultra-high fat diet group (CH-HF). The mice are fed with normal diet group (Chow) until 8 weeks old and then are fed with different high fat diet, respectively being HF feed (HF formula: 21.2% fat, 48.7% carbohydrate, 17.3% protein, and 0.25% cholesterol), H-HF feed (H-HF formula: 21.2% fat, 48.7% carbohydrate, 17.3% protein, and 1.25% cholesterol), and CH-HF feed (CH-HF formula: 21.2% fat, 48.7% carbohydrate, 17.3% protein, 1.25% cholesterol, and 0.5% cholic acid). After 8 weeks of treatment, collecting the blood of the mice, detecting the body weight, heart weight, spleen weight and blood lipids of the mice, and isolating the mice aorta for oil red O staining so as to quantify the atherosclerotic plaque content.

Figure 7:
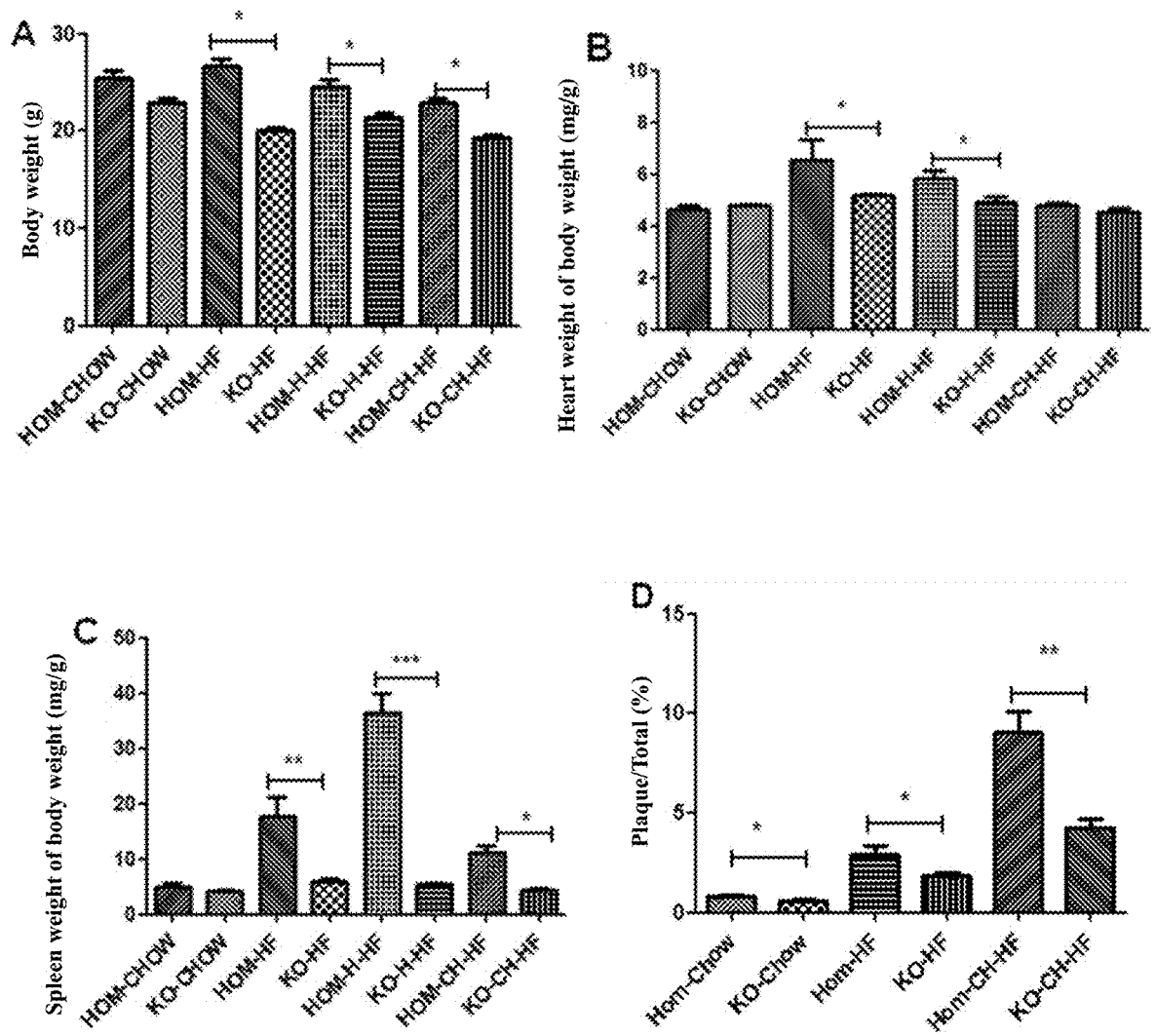
FIG. 7 is a graph showing the effect of hyperlipidemia on atherosclerotic lesions studied by using the mouse according to the present invention. A is the effect of different diets on the body weight of mice; B is the effect of different high-fat diet on the heart weight of mice; C is the effect of different high-fat diet on the spleen of mice; and D is the atherosclerosis of mice induced by different high-fat diets. Chow refers to normal diet group; HF, H-HF, and CH-HF refer to different high-fat diet groups; Hom refers to homozygous mice; and KO refers to ApoE knockout mice. *$P<0.05$, $P<0.01$, *$P<0.001$.

The results are shown in FIG. 6A to FIG. 6D. It is indicated that the high fat diet could induce the triglyceride, cholesterol and low-density lipoprotein cholesterol contents in the blood of homozygous mice to have high level similar to traditional lipid-deficient mice ApoE knockout mouse (KO), whereas the high-density lipoprotein cholesterol in the blood of homozygous mice is much higher than that of ApoE knockout mice (KO); this indicates that different high-fat diets could induce hyperlipidemia in blood of homozygous mice. Unlike traditional lipid-deficient mice, the homozygous mice, since having cholesterol reverse transport defects, would suffer high level accumulation of high-density lipoprotein cholesterol in the blood of mice owing to high-fat diets. In addition, as shown in FIGS. 7A and 7B, different high-fat diets render homozygous mice to have body weight higher than traditional lipid-metabolized mice, and thus induce larger hearts of homozygous mice. As shown in FIG. 7C, different high-fat diets induce bigger spleen of homozygous mice, indicating that more inflammatory responses would occur in mice. As shown in FIG. 7D, according to the quantitation of the atherosclerotic plaques of homozygous mice, it is found that, after being fed with normal diet until 16 weeks old, the homozygous mice have atherosclerotic plaques content higher than ApoE knockout mice; this indicates that increased content of cholesterol in the diet of mice would accelerate the formation of atherosclerotic plaques in homozygous mice, and the atherosclerotic plaques in homozygous mice as formed are much higher than that of ApoE knockout mice, showing that homozygous mice are more likely to be induced atherosclerotic plaque lesions.

Example 8 Mice According to the Present Invention for the Study Related to Hypertension The mice are divided into 3 groups for experiments, wild-type mice (Wt), homozygous mice (Hom) and heterozygous mice (Het), with each group having 15 mice. The mice are fed with normal diet (Chow) until 8 weeks old, and are administrated tetracycline analog doxycycline (1 to 2 mg/ml) with water. The blood pressure changes of mice are measured periodically. The method for measuring the blood pressure of mice is the method of non-invasive tail pressure measurement [9] (iiTC Life Science, Woodland Hills, CA), wherein the mice are fixed in the sleeve and stay quiet in the sleeve for 10 minutes. Then the instrument is operated to measure the blood pressure at the tail of mice using infrared spectroscopy, three measurements are made for each operation, and the average is taken. Mice blood is collected, and body weight, heart weight, spleen weight, blood lipids and blood pressure of mice are measured.

Figure 8:
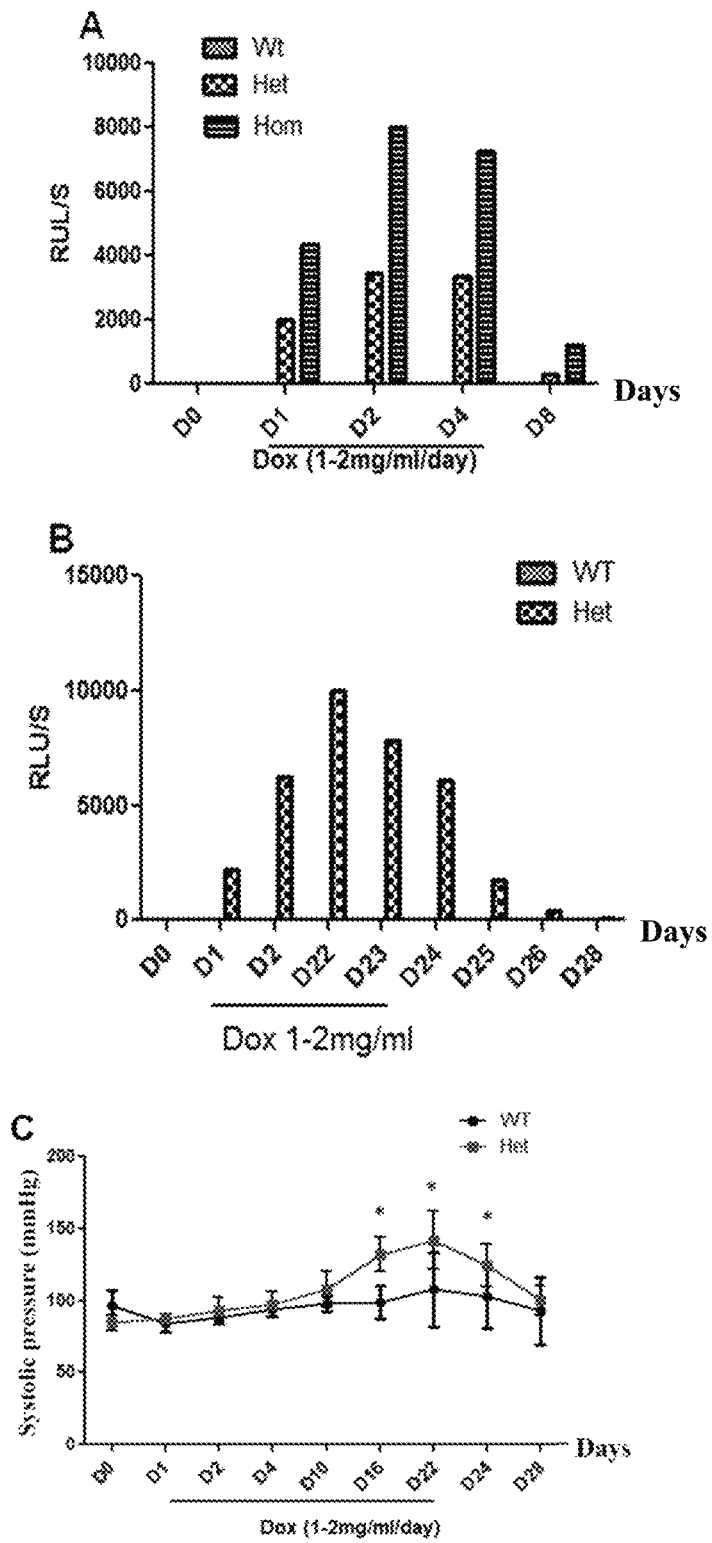
FIG. 8 is a graph showing that the mice according to the present invention has hypertension caused by induction, and showing the relationship between the induced hypertension and Gaussian luciferase fluorescence. A is the detection result of Gaussian luciferase of mice blood before administrating doxycycline, administrating doxycycline for 4 days, and stopping doxycycline for 4 days; Figure B is the detection result of Gaussian luciferase of mice blood before administrating doxycycline, administrating doxycycline for 23 days, and stopping doxycycline for 5 days; Figure C is the detection result of blood pressure of mice before administrating doxycycline, administrating doxycycline for 23 days, and stopping doxycycline for 5 days. *$P<0.05$. Hom refers to homozygous mice, Het refers to heterozygous mice, and Wt refers to wild-type mice.
Figure 9:
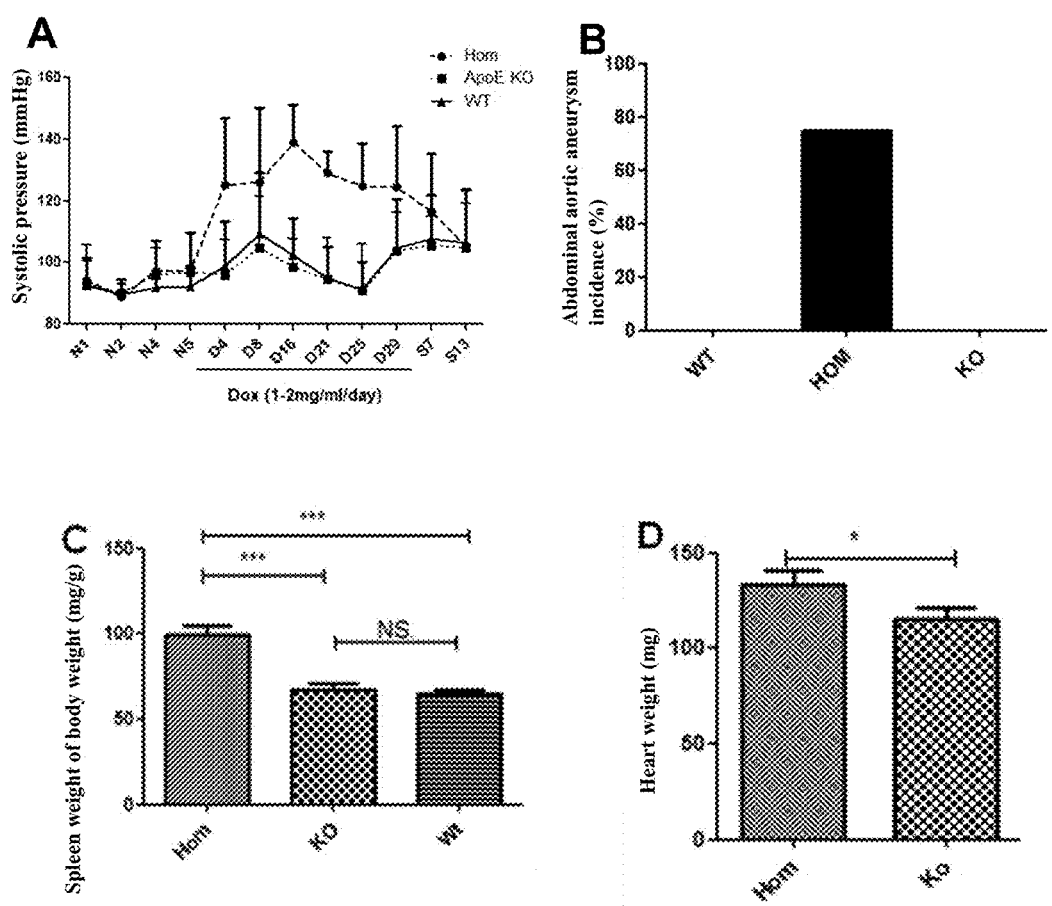
FIG. 9 shows related symptoms caused by hypertension inducted in mice according to the present invention. A is the detection result of blood pressure of mice 5 days before administrating doxycycline, administrating doxycycline for 29 days, and stopping doxycycline for 13 days; B is the detection result of mouse abdominal aortic aneurysm; C is the detection result of the spleen weight ratio of mice; D is the heart weight of mice. *$P<0.05$; $P<0.01$; *$P<0.001$; NS refers to no difference. Hom refers to homozygous mouse, KO refers to ApoE knockout mice, and Wt refers to wild-type mice.

As shown in FIG. 8A, it is detected that Gaussian luciferase was produced in the body of mice on the first day of adding doxycycline (Dox) into the drinking water of homozygous and heterozygous mice (detecting being made by using Gauss Fluorescein Mei kit, SPGA-G010, regenerative gene, Guangzhou), and the content of Gauss luciferase in mice decreases 4 days after stop administrating the drug. Since Gaussian luciferase and angiotensin II are produced by co-expression in homozygous and heterozygous mice, it indicates that Dox could induce the mice to produce angiotensin II, and the level of angiotensin II can be monitored by detecting Gauss luciferase. As shown in FIG. 8B to FIG. 8C, after continuously adding Dox into the drinking water of the mice for 23 days, high levels of Gauss luciferase are continuously produced in the body of heterozygous mice (Het), and the blood pressure gradually increases, then stopping administrating the drug, the Gaussian luciferase produced in the body of heterozygous mice (Het) gradually decreases within 5 days and disappeared eventually, and the blood pressure gradually returned to normal. As shown in FIG. 9A in combination with FIG. 8A, after continuously adding Dox into the drinking water of the mice for 29 days, high levels of Gauss luciferase are continuously produced in the body of homozygous mice (Hom), and the blood pressure gradually increases, then stopping administrating the drug, the Gaussian luciferase produced in the body of homozygous mice (Hom) gradually decreases within 13 days and disappeared eventually, and the blood pressure gradually returned to normal. In addition, as shown in FIG. 9B to FIG. 9D, the spleen and heart weight of homozygous mice (Hom) are higher than those of ApoE knockout mice of the same experimental batch, and long-term hypertension induced homozygous mice have abdominal aortic aneurysms. It is indicated that hypertensive symptoms could be easily and effectively induced in homozygous and heterozygous mice; such induction is controllable and can be monitored by Gauss luciferase, thereby benefiting hypertension-related research.

Example 9 Mice According to the Present Invention for the Study of Cardiovascular Related Diseases Induced by Hypertension The mice are divided into 7 groups for experiments, wild-type mice (Wt), homozygous mice (Hom) and heterozygous mice (Het), and ApoE knockout mice (KO), with each group having 15 mice. The mice are fed with normal diet (Chow) until 8 weeks old, are administrated tetracycline analog doxycycline (Dox) (1 to 2 mg/ml) with water, and are continued to be fed with laboratory common diet (Chow) for 4 weeks; the homozygous mice (Hom) are fed with normal diet (Chow) until 8 weeks old, are administrated tetracycline analog doxycycline (1 to 2 mg/ml) with water, and are continued to be fed with high-fat diet (HFD) for 4 weeks; the homozygous mice (Hom) are fed with normal diet (Chow) until 8 weeks old, and are continued to be fed with high-fat diet (HFD) for 4 weeks. Detecting the systolic pressure of the mice before being killed; killing the mice and collecting the plasma to detect cholesterol (CHOL) concentration; collecting the ascending aorta of the mice to stain with oil red O; collecting the hearts for frozen section, and staining the frozen sections with oil red O.

Figure 10:
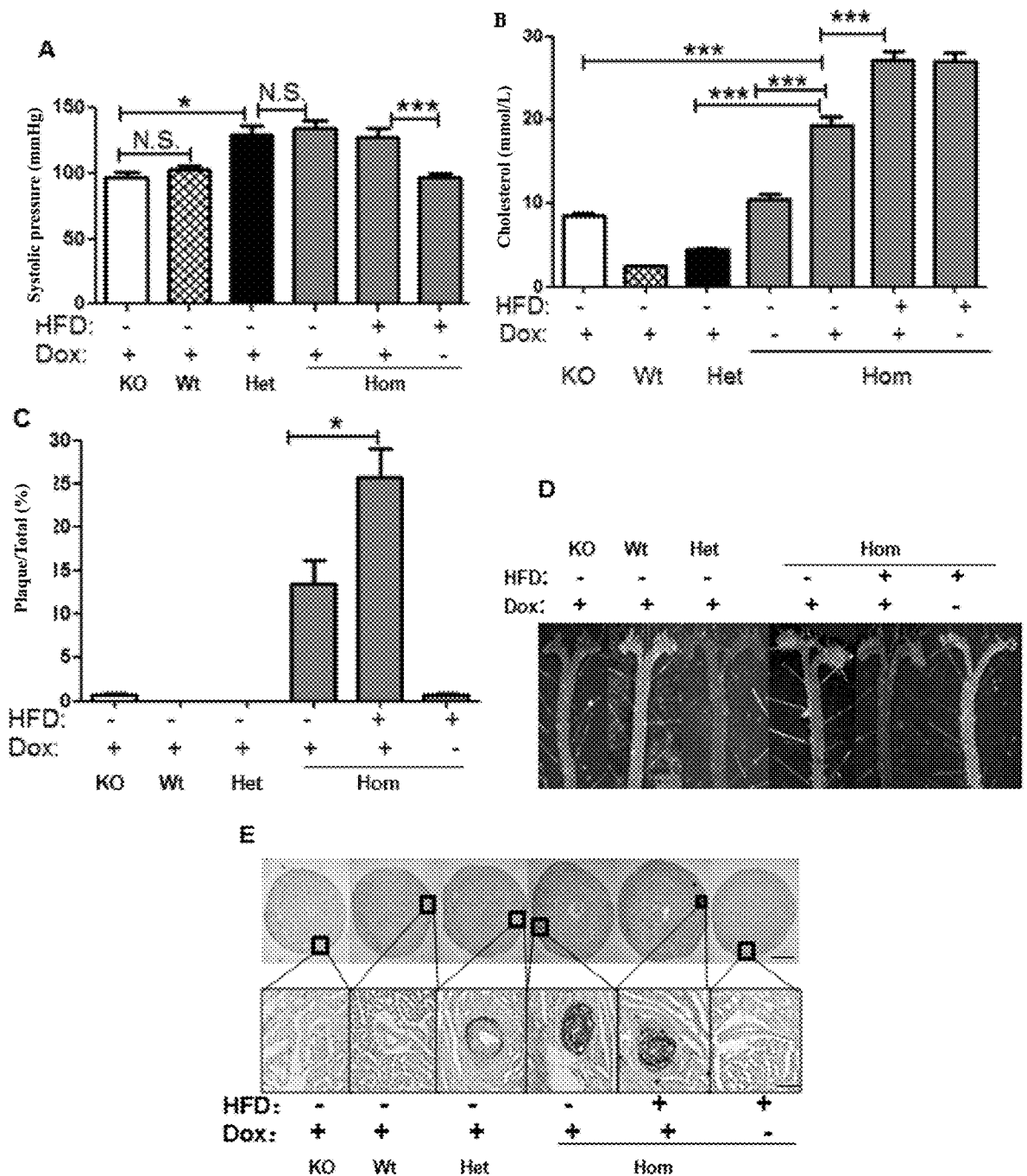
FIG. 10 is a diagram showing the study of hypertension-induced cardiovascular-related diseases with the mice according to the present invention. A is the systolic blood pressure of mice after 4 weeks of treatment; B is the detection of plasma cholesterol concentration of mice after 4 weeks of treatment; C is the quantification of ascending aortic atherosclerotic plaques of mice after 4 weeks of treatment; D is the display of the ascending aortic atherosclerotic plaque of mice after 4 weeks of treatment; E is the display under microscope of mice heart slice with oil red O stained (bar=800 μm) and partial enlargement thereof (bar=50 μm) after 4 weeks of treatment. *$P<0.05$; $P<0.01$; *$P<0.001$; NS refers to no difference. HFD refers to high-fat diet, Dox refers to supplying doxycycline by drinking water, KO refers to an ApoE knockout mice, Wt refers to wild-type mice, Het refers to a heterozygous mice according to the present invention, and Hom refers to homozygous mice according to the present invention.
Figure 11:
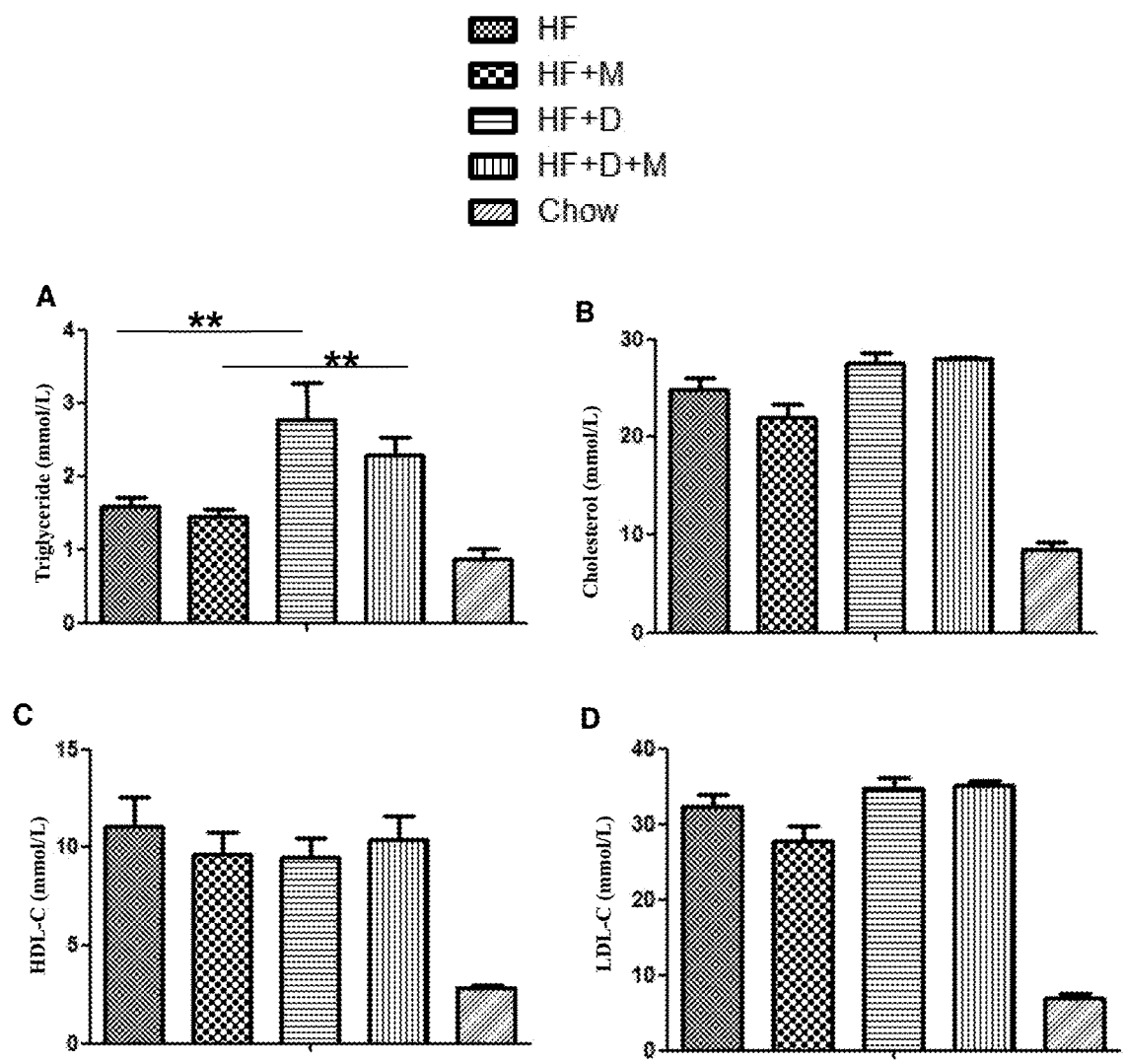
FIG. 11 is a graph showing the study on the cardiovascular related diseases caused by the combination of hypertension and hyperlipidemia using the mice according to the present invention. A to D show the results of four blood lipid of mice. Chow refers to normal diet group, HF refers to high-fat diet, D refers to being administrated doxycycline, and M refers to injecting methotrexate. **$P<0.01$.

As shown in FIG. 10A, both homozygous mice and heterozygous mice could be induced by Dox to have high systolic pressure; as shown in FIG. 10B, feeding with the same normal diets, Dox made homozygous (Hom) mice have higher cholesterol concentration in the plasma than that of ApoE knockout (KO) mice; this indicates that AngII causes hypercholesterolemia in homozygous mice. Similarly, high-fat diet also causes hypercholesterolemia in homozygous mice. As shown in FIG. 10C and FIG. 10D, the aorta of homozygous mice is induced to accelerate the formation of atherosclerosis after 4-week of Dox treatment, but for only 4 weeks of Dox treatment, the aorta of heterozygous mice would not be induced to accelerate the formation of atherosclerosis. FIG. 10E shows that homozygous mice would be induced to have severe atherosclerosis of coronary arteries in the heart after 4 weeks of Dox treatment. In this case, it is possible to occlude the coronary arteries, which would cause insufficient blood supply to the heart and myocardial infarction, and would cause heart failure if lasting for a long term. For only 4 weeks of Dox treatment, it would not induce atherosclerotic plaque in the coronary artery of heterozygous mice, but would thicken and remodel the coronary artery of heterozygous mice, with fat deposition in the coronary vascular adventitia.

The inventors have also studied the effects of hypertension on coronary artery lesions in mice of different genders, and the results show that the effect of hypertension on coronary artery lesions was similar in female and male mice (data not shown). In conclusion, hypertension dramatically increases coronary atherosclerosis in the case of dyslipidemia.

Example 10 Mice According to the Present Invention for Studying Cardiovascular Related Diseases Caused by the Combination of Hypertension and Hyperlipidemia, and Drug Therapy and the Mechanism Thereof Homozygous mice, divided into 5 groups, are to fed with normal diet (Chow), high-fat diet (HF), high-fat diet plus boostin (HF+D), high-fat diet plus methotrexate (MTX) (HF+M), and high-fat diet plus boostin and methotrexate (HF+D+M). Methotrexate is an anti-inflammatory drug that can down-regulate IL-6, ICAM-1, E-selectin, VCAM-1 expressions and other expressions, etc. Clinically, low doses of methotrexate could reduce cardiovascular risk in patients suffering from long-term inflammatory diseases such as rheumatoid arthritis [10]. Homozygous mice are fed with normal diet (Chow) until 8 weeks old, and are fed with high fat diet HF (HF formula: 21.2% fat, 48.7% carbohydrate, 17.3% protein, and 0.25% cholesterol) for 8 weeks. The mice are divided in to groups, with each group having 15 mice. The HF group is fed with high-fat diet, and is injected with 100 μl of physiological saline weekly. The HF+M group is fed with high-fat diet, and is injected with methotrexate at a dose of 1 mg/kg once a week. The HF+D group is fed with high-fat diet and 1-2 mg/ml of doxycycline together with drinking water, and is injected with 100 μl of physiological saline weekly. The HF+D+M group is fed with high-fat diet, injected with methotrexate at a dose of 1 mg/kg once a week, and fed with doxycycline at 1-2 mg/ml together with drinking water. The blood pressure changes of the mice are periodically detected, and the data such as blood, blood lipids, blood pressure and death data etc. of the mice are collected.

Figure 12:
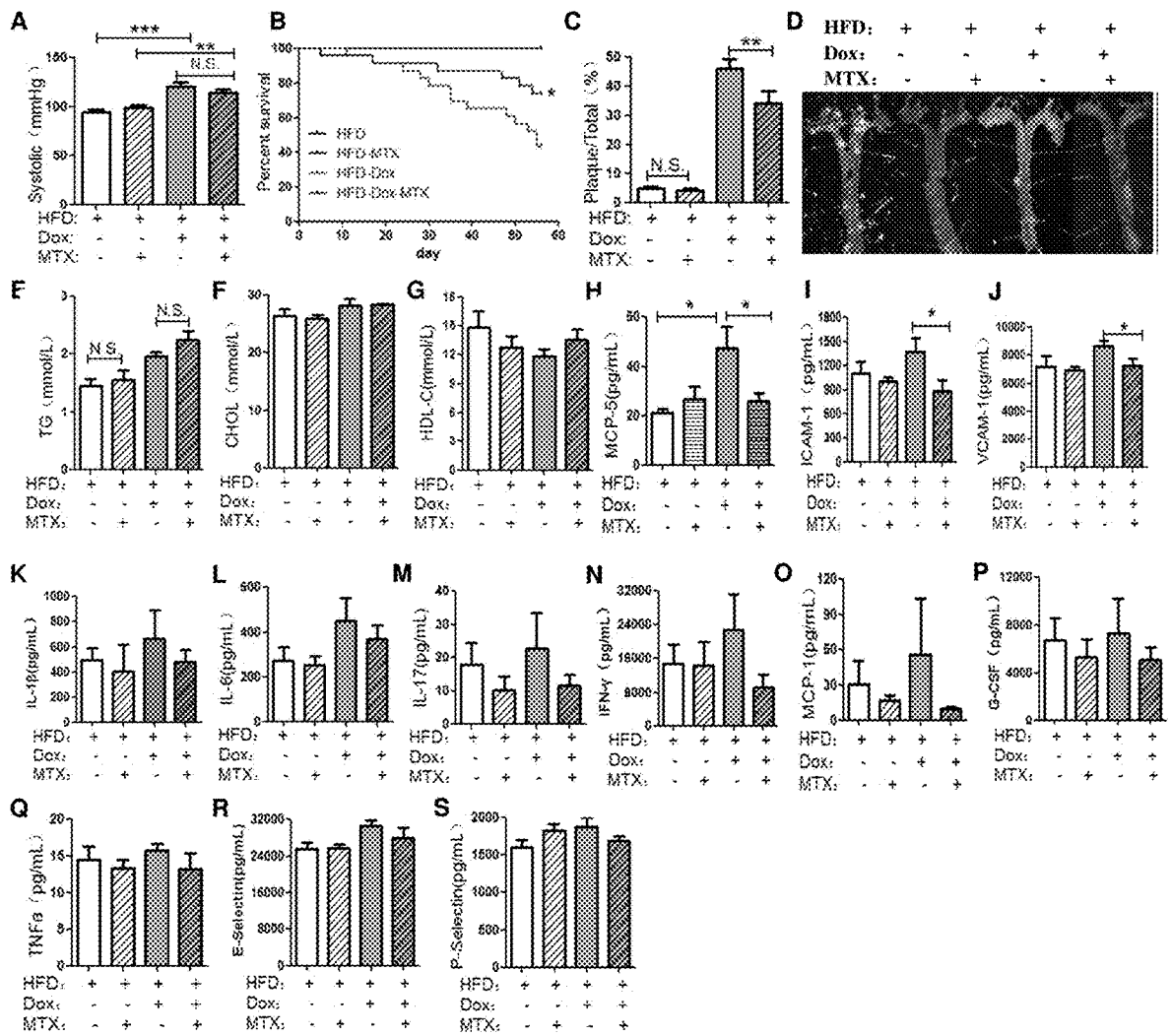
FIG. 12 shows the study of drug treatment for the cardiovascular related diseases caused by the combination of hypertension and hyperlipidemia using the mice according to the present invention. A is the blood pressure of mice of each group; B is the survival curve of mice of each group; C is the quantification of ascending aortic atherosclerotic plaques of mice of each group; D is the display of ascending aortic atherosclerotic plaque of mice of each group; E is the total triglyceride (TG) concentration in plasma of mice in each group; F is the concentration of total cholesterol (CHOL) in plasma of mice in each group; G is the concentration of high density lipoprotein cholesterol (HDL-C) in plasma of mice in each group; H to S is the detection of various cytokines in plasma of mice in each group, MCP-5 is monocyte chemotactic factor 5, ICAM-1 is intercellular adhesion molecule-1, VCAM-1 is blood vessel cell adhesion molecule-1, IL-β is interleukin-β, IL-6 is interleukin 6, IL-17 is interleukin 17, IFN-γ is dry element γ, MPC-1 is monocyte chemotactic factor 1, G-CSF is granulocyte colony-stimulating factor, TNFα is tumor necrosis factor α, E-selectin is E-selectin, and P-Selectin is P-selectin. *$P<0.05$; $P<0.01$; *$P<0.001$. HFD refers to high-fat diet, Dox refers to being administrated doxycycline, and MTX refers to being injected with methotrexate.

As shown in FIGS. 11A to 11D, hypertension combined with a high-fat diet induce higher accumulation of triglycerides in the blood of mice. The inventors, using homozygous mice, have studied the effects of methotrexate (MTX) (an anti-inflammatory drug) on cardiovascular. Male homozygous mice are fed with HF diet with/without the addition of doxycycline (Dox), and are further randomized by intraperitoneal injection of MTX or control (vector) weekly. It is found that the mice which are fed with doxycycline together with drinking water show hypertensive symptoms. MTX would not alter the blood pressure of the mice (FIG. 12A). Hypertension combined with a high-fat diet induced higher mortality of mice, but if injected with methotrexate weekly, the survival rate of mice is increased at 8 weeks of co-administration (74% versus 43%, FIG. 12B). Although MTX would not affect atherosclerosis in hypertensive mice fed with HF diet, it reduces atherosclerotic lesions of hypertensive mice fed with HF diet for 8 weeks (46% vs. 34% P<0.05, FIGS. 12C-D). In addition, an inflammation increase is observed in induced hypertension, and the administration of MTX would significantly reduce the plasma concentration in hypertensive mice in terms of monocyte chemoattractant protein (MCP)-5, intercellular adhesion molecule-1 and vascular cell adhesion molecules, but would not produce any effect in homozygous mice having normal blood pressure (FIGS. 12H-J). Comparing with the control group, in the induced hypertensive MTX group, Cytokines IL-1β, IL-6 and IL-17, interferon-γ, MCP-1, granulocyte colony-stimulating factor, tumor necrosis factor-α, E-selectin and P-selectin have decreased level (FIGS. 12K-S). These data indicate that in homozygous mice with dyslipidemia and hypertension, MTX may prevent death and atherosclerotic lesions resulted from cardiovascular disease death by reducing the hypertension enlarged inflammation.

Example 11 Mice According to the Present Invention for Studying Effect of Hypertension on the Forming of Thrombosis Homozygous mice (Hom) and wild-type mice (Wt), as controls, are divided into normal diet group (Chow) and a doxycycline group (Dox) respectively, with each group having 15 mice. The mice are fed with normal diet group until 8 weeks old, and are fed with tetracycline analog doxycycline (1 to 2 mg/ml) together with water. The blood pressure changes in mice are periodically measured. The blood of mice is collected, and the body weight, heart weight, blood pressure, etc. are measured. Vascular thrombosis forming experiment is performed after five days of feeding doxycycline. Mice were injected with 50 mg/kg of Rose Bengal, the carotid artery of the mice was irradiated with laser until forming thrombosis, and the forming time of thrombosis was recorded.

Figure 13:
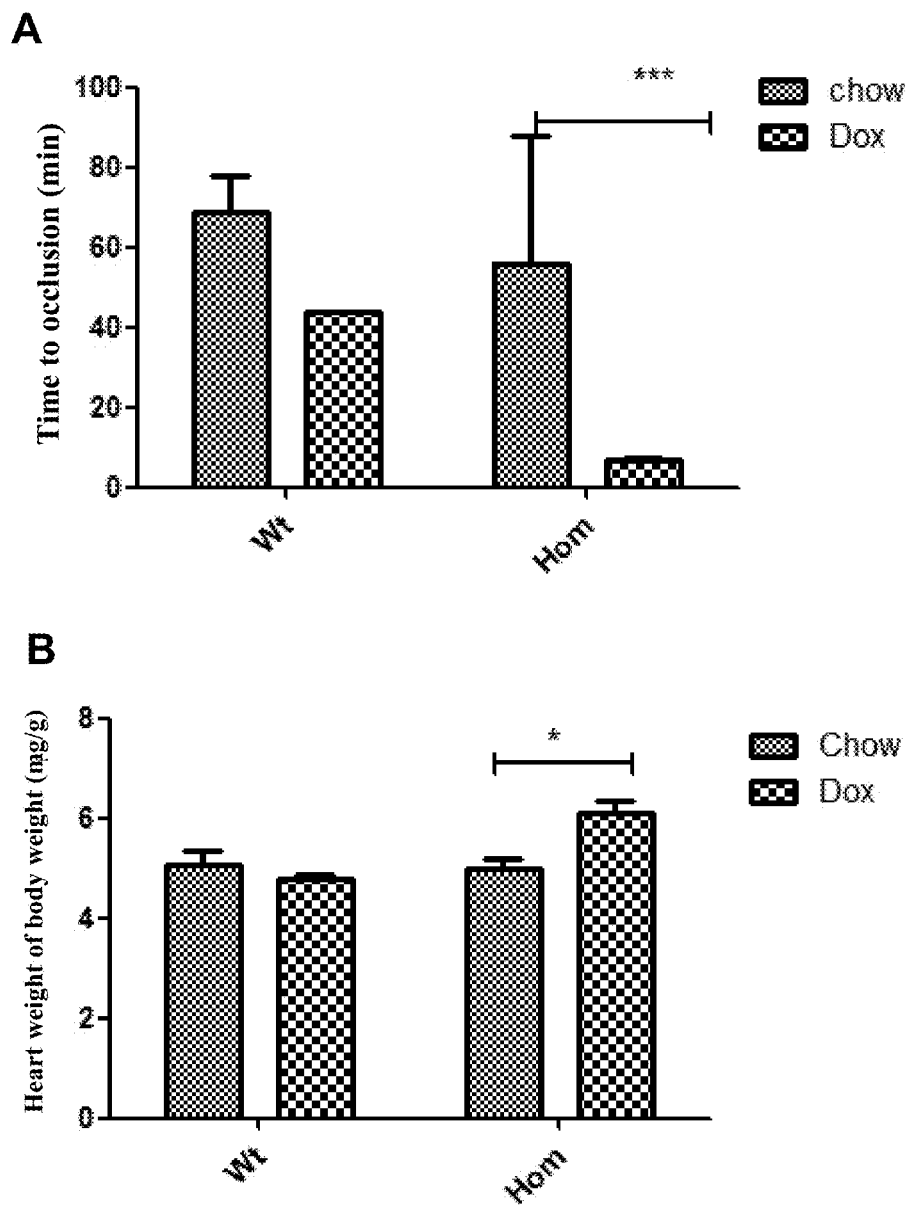
FIG. 13 is a graph showing the study on thrombus formation affected by hypertension using the mice according to the present invention. A is the time for thrombus formation; B is the statistics of heart weight ratio of mice. Wt refers to wild-type mice, Hom refers to homozygous mouse. Chow refers to normal diet; Dox refers to the group of being administrated doxycycline. *$P<0.05$; ***$P<0.001$.

As shown in FIG. 13A to FIG. 13B, it is found that the homozygous mice, after 5 days of inducing hypertension with doxycycline, have faster-formed carotid artery thrombus. Meanwhile, the homozygous mice have lager ratio of heart weight owing to long-term hypertension. This indicates that short-term hypertension could accelerate the forming of thrombus of mice and aggravate the heart load of mice.

Example 12 Mice According to the Present Invention for Studying Effect of Hyperlipidemia on the Forming of Thrombosis Homozygous mice (Hom) and ApoE knockout mice (KO), as controls, are divided into normal diet group (Chow), higher fat diet group (H-HF) and ultra-high fat diet group (CH-HF), with each group having 15 mice. The mice are fed with normal diet group (Chow) until 8 weeks old and then are fed with different high fat diet, respectively being H-HF feed (H-HF formula: 21.2% fat, 48.7% carbohydrate, 17.3% protein, and 1.25% cholesterol), and CH-HF feed (CH-HF formula: 21.2% fat, 48.7% carbohydrate, 17.3% protein, 1.25% cholesterol, and 0.5% cholic acid). The blood of mice is collected, and the body weight, heart weight, spleen weight and blood lipid etc. are measured. Vascular thrombosis forming experiment was performed after 8 weeks of treatment. Mice were injected with 50 mg/kg of Rose Bengal, the carotid artery of the mice was irradiated with laser until forming thrombosis, and the forming time of thrombosis was recorded.

Figure 14:
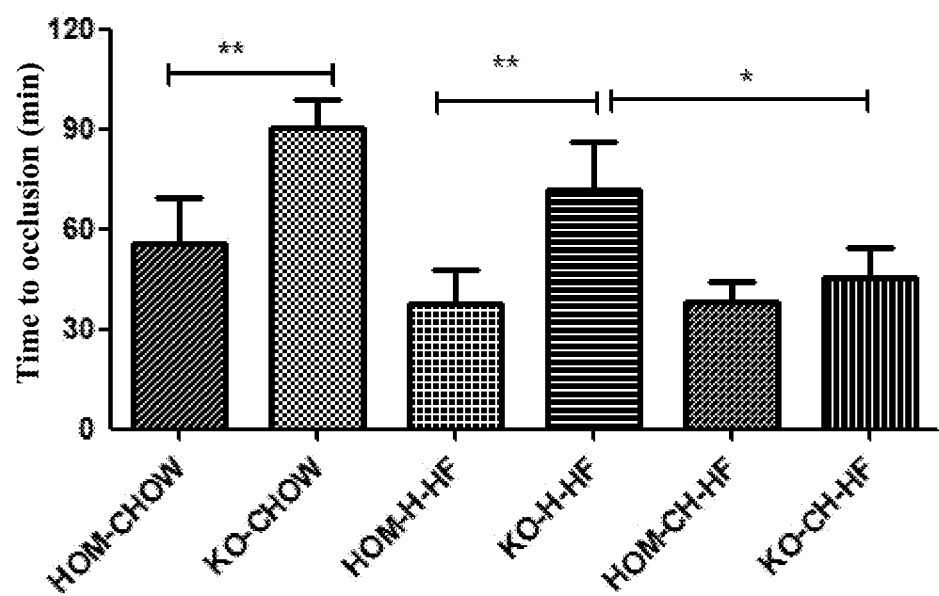
FIG. 14 is a graph showing the study on thrombus formation affected by hypertension using the mice according to the present invention. Hom refers to homozygous mice; KO refers to ApoE knockout mice. Chow refers to normal diet; H-HF and CH-HF refer to different high-fat diets. *$P<0.05$, **$P<0.01$.

As shown in FIG. 14, it is found that homozygous mice, as compared with traditional lipid metabolism deficient mice, have faster-formed thrombosis in case of being subjected to the same diet treatment, accelerating the forming of thrombosis in mice.

Figure 15:
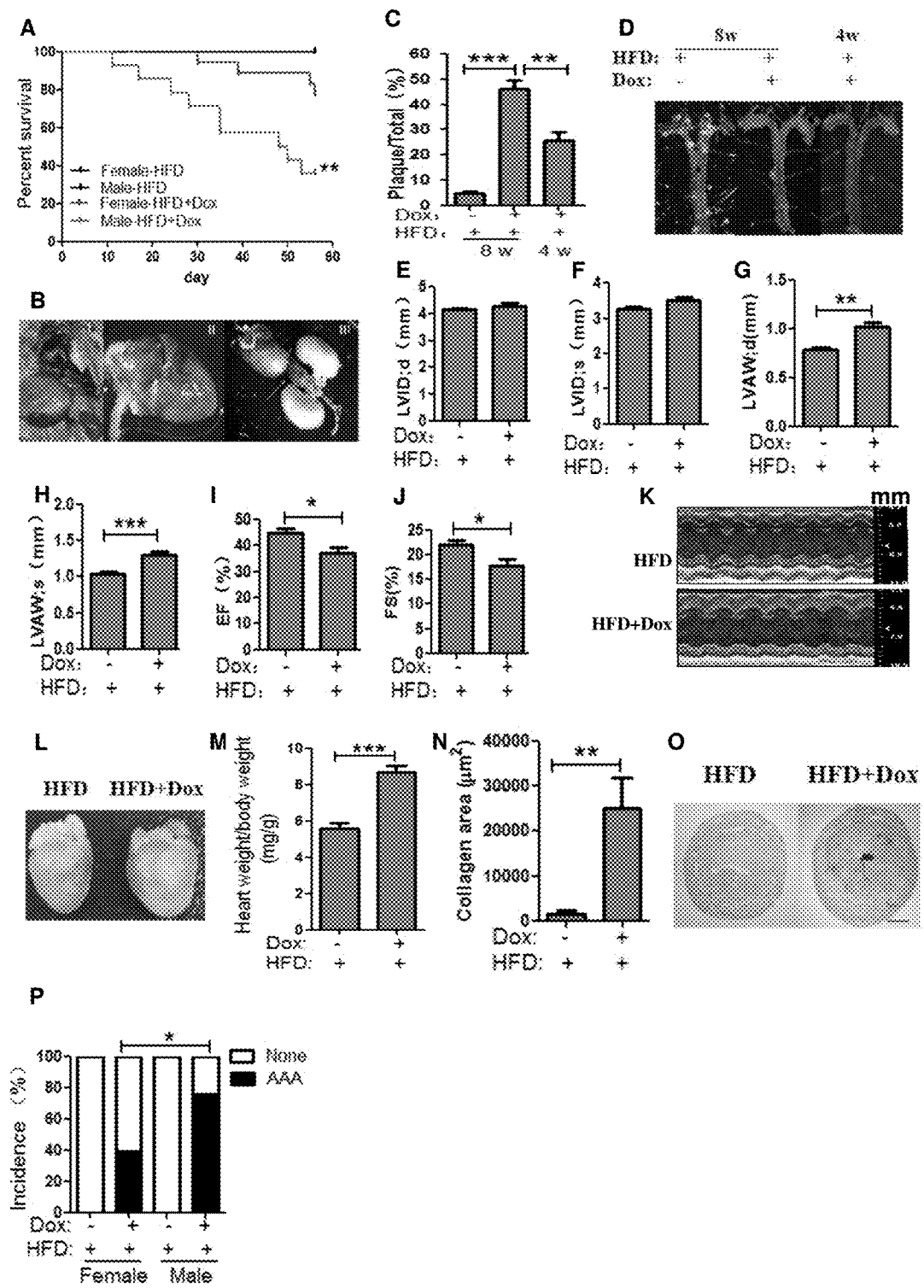
FIG. 15 is a graph showing the study on cardiovascular-related diseases caused by the combination of hypertension and hyperlipidemia using mice of different sexes. A is the Kaplan-Meier survival curve of mice; B is the anatomy of sudden death mouse; C is the quantitative result of the mice atherosclerotic lesion; D is the representative red oil O staining of aorta; E to J are the Echocardiographic parameters of mice after 4 weeks of administration; K is a representative M-type short-axis view of left ventricular of mice; L is a representative heart picture of mice; M is the ratio of heart weight to body weight of mice; N is the comparison of collagen area in the myocardium of mice; O is a representative picture of Sirius red stained myocardium (bar=800 μm). Dox refers to being administrated doxycycline, HFD refers to high-fat diet, *P<0.05; P<0.01; *P<0.001. 8 w refers to 8 weeks, 4 w refers to 4 weeks, LV refers to left ventricle, ID refers to inner diameter, d refers to the diastolic phase, s refers to the systolic phase, AW refers to the thickness of the anterior wall, EF refers to the ejection fraction, and FS refers to the fractional shortening.

Example 13 Mice of Different Genders According to the Present Invention for Studying Cardiovascular Related Diseases Caused by the Combination of Hypertension and Hyperlipidemia The prolonged effect of the combination of dyslipidemia and hypertension was studied in homozygous mice. The mice were fed with HF feed and water containing doxycycline (Dox) for 8 weeks. After starting the experiment, the mice, especially the male ones, suffer from sudden death. The male mice have a survival rate of 36%, and the female mice have a survival rate of 78%, after being fed with HF feed and Dox for 8 weeks; all the mice that are fed HF feed survive (FIG. 15A). Necropsy shows that the earlier-dead mice are suffered from abdominal aorta and/or ascending aorta rupture in the, and the late-dead animals suffer from severe myocardial infarction, coronary atherosclerosis, and aortic aneurysm (FIG. 15B).

Owing to the high mortality of male mice that are fed with HF feed together with Dox, female mice are used for atherosclerosis quantification. As compared with only feeding with HF feed, combined feeding significantly promotes the development of atherosclerosis: after 4 weeks and 8 weeks of combined feeding, the arterial lesion coverage increased to 25.7% and 46.1% respectively, compared with the mild lesion development (4.7%) after 8 weeks of only feeding HF diet (FIGS. 15C-15D).

Since all female mice are alive after 4 weeks of feeding HF feed and Dox, they were used to assess cardiac function at this time point. Increased wall thickness of left ventricular and decreased cardiac function are detected by echocardiographic analysis (EF and FS) (FIGS. 15E to 15K). Hypertensive induction resulted in increased ratio of heart weight to body weight (5.6 mg/g versus 8.7 mg/g, P<0.001, FIGS. 15L to 15M) and collagen deposition (24.97×103 vs 1.11× 103 μm2, P<0.001, FIGS. 15N to 15O), as compared with mice only fed with HF feed. Therefore, the combination of dyslipidemia and hypertension has greatly prompted the complications of middle and late atherosclerosis of CAD.

After four weeks of adding Dox in drinking water and feeding HF feed, the survived mice are subjected to further characterizing aortic aneurysms. These mice suffer from abdominal aortic aneurysm (AAA), wherein the males have incidence significantly higher than that of females (76% vs 39%, chi-square test, P=0.0247, FIG. 15P). In homozygous mice fed with HF feed without feeding Dox, abdominal aortic aneurysms are not observed.

REFERENCES

1. Plump A S, Smith J D, Hayek T, Aalto-Setala K, Walsh A, Verstuyft J G, Rubin E M, Breslow J L. Severe hypercholesterolemia and atherosclerosis in apolipoprotein e-deficient mice created by homologous recombination in es cells. Cell. 1992; 71:343-353.
2. Rigotti A, Trigatti B L, Penman M, Rayburn H, Herz J, Krieger M. A targeted mutation in the murine gene encoding the high density lipoprotein (hdl) receptor scavenger receptor class b type i reveals its key role in hdl metabolism. Proceedings of the National Academy of Sciences of the United States of America. 1997; 94:12610-12615.
3. Santander N G, Contreras-Duarte S, Awad M F, Lizama C, Passalacqua I, Rigotti A, Busso D. Developmental abnormalities in mouse embryos lacking the hdl receptor sr-bi. Human molecular genetics. 2013; 22:1086-1096.
4. Yesilaltay A, Daniels K, Pal R, Krieger M, Kocher O. Loss of pdzkl causes coronary artery occlusion and myocardial infarction in paigen diet-fed apolipoprotein e deficient mice. PloS one. 2009; 4:e8103.
5. Braun A, Trigatti B L, Post M J, Sato K, Simons M, Edelberg J M, Rosenberg R D, Schrenzel M, Krieger M. Loss of sr-bi expression leads to the early onset of occlusive atherosclerotic coronary artery disease, spontaneous myocardial infarctions, severe cardiac dysfunction, and premature death in apolipoprotein e-deficient mice. Circulation research. 2002; 90:270-276. Circulation research. 2002; 90:270-276.
6. Cha J, Ivanov V, Ivanova S, Kalinovsky T, Rath M, Niedzwiecki A. Evolution of angiotensin ii-mediated atherosclerosis in apoe ko mice. Molecular medicine reports. 2010; 3:565-570.
7. Heo H J, Yun M R, Jung K H, Lee J Y, Park J Y, Lee S J, Bae S S, Lee W S, Kim C D. Endogenous angiotensin ii enhances atherogenesis in apoprotein e-deficient mice with renovascular hypertension through activation of vascular smooth muscle cells. Life sciences. 2007; 80:1057-1063.
8. Chu Y, Lund D D, Doshi H, Keen H L, Knudtson K L, Funk N D, Shao J Q, Cheng J, Hajj G P, Zimmerman K A, Davis M K, Brooks R M, Chapleau M W, Sigmund C D, Weiss R M, Heistad D D. Fibrotic aortic valve stenosis in hypercholesterolemic/hypertensive mice. Arteriosclerosis, thrombosis, and vascular biology. 2016; 36:466-474.
9. Shen M, Lee J, Basu R, Sakamuri S S, Wang X, Fan D, Kassiri Z. Divergent roles of matrix metalloproteinase 2 in pathogenesis of thoracic aortic aneurysm. Arteriosclerosis, thrombosis, and vascular biology. 2015; 35:888-898.
10. Tousoulis D, Oikonomou E, Economou E K, Crea F, Kaski J C. Inflammatory cytokines in atherosclerosis: Current therapeutic approaches. European heart journal. 2016; 37:1723-1732.

The invention claimed is:

1. A genetically engineered non-human mammal, wherein the non-human mammal has a genome with the ApoE gene therein being disrupted so that ApoE is not expressed, and wherein the genome comprises (i) an exogenous nucleotide sequence encoding an siRNA against scavenger receptor class B type I (SR-BI), the exogenous nucleotide sequence being operably linked to an ApoE gene promoter, and (ii) one or more exogenous nucleotide sequences encoding a vasoconstrictor operably linked to an inducible promoter, wherein the exogenous nucleotide sequence encoding the siRNA and the one or more exogenous nucleotide sequences encoding the vasoconstrictor are inserted into the ApoE gene, and wherein the inserted exogeneous nucleotide sequence encoding the siRNA and the inserted one or more exogenous nucleotide sequences encoding the vasoconstrictor disrupt the ApoE gene so that ApoE is not expressed, wherein expression of the siRNA knocks down SR-BI expression in the liver of the non-human mammal, wherein the coding sequence of the siRNA has a homology of 100% to the sequence as shown in SEQ ID NO. 4, wherein the vasoconstrictor is angiotensin II, wherein the inducible promoter is a chemical-inducible promoter, and the chemical inducible promoter is a tetracycline-inducible promoter, and wherein the homozygous form of the genetically engineered non-human mammal displays hypercholesterolemia, hyperlipidemia, increase arteriosclerotic lesion formation, and hypertension as compared to the genetically engineered non-human mammal comprising a disruption of the ApoE gene so that ApoE is not expressed.

2. The non-human mammal according to claim 1, wherein the exogeneous nucleotide sequence encoding the siRNA has a flanking that comprises an element of an FLP/FRT recombinase system, and the element is an FRT sequence.

3. The non-human mammal according claim 1, wherein the angiotensin II is co-expressed with a detectable tag selected from luciferase, Gauss luciferase, firefly luciferase, sea cucumber luciferase, and fluorescent proteins.

4. Cell, organ or tissue of a genetically engineered non-human mammal, wherein the non-human mammal has a genome with the ApoE gene therein being disrupted so that ApoE is not expressed, and wherein the genome comprises (i) an exogenous nucleotide sequence encoding an siRNA against scavenger receptor class B type I (SR-BI), the exogenous nucleotide sequence being operably linked to an ApoE gene promoter, and (ii) one or more exogenous nucleotide sequences encoding a vasoconstrictor operably linked to an inducible promoter, wherein the exogeneous nucleotide sequence encoding the siRNA and the one or more exogenous nucleotide sequences encoding the vasoconstrictor are inserted into the ApoE gene, and wherein the inserted exogeneous nucleotide sequence encoding the siRNA and the inserted one or more exogenous nucleotide sequences encoding the vasoconstrictor disrupt the ApoE gene so that ApoE is not expressed, wherein expression of the siRNA knocks down SR-BI expression in the liver of the non-human mammal, wherein the coding sequence of the siRNA has a homology of 100% to the sequence as shown in SEQ ID NO. 4, wherein the vasoconstrictor is angiotensin II, wherein the inducible promoter is a chemical-inducible promoter, and the chemical inducible promoter is a tetracycline-inducible promoter, and wherein the homozygous form of the genetically engineered non-human mammal displays hypercholesterolemia, hyperlipidemia, increase arteriosclerotic lesion formation, and hypertension as compared to the genetically engineered non-human animal comprising a disruption of the ApoE gene so that ApoE is not expressed.

5. The cell, organ or tissue according to claim 4, wherein the exogeneous nucleotide sequence encoding the siRNA has a flanking that comprises the element of an FLP/FRT recombinase system, and the element is an FRT sequence.

6. The cell, organ or tissue according to claim 4, wherein the angiotensin II is co-expressed with one tag selected from luciferase, Gauss luciferase, firefly luciferase, sea cucumber luciferase, and fluorescent proteins.

7. The non-human mammal according to claim 3, wherein the tag is Gauss luciferase.

8. The non-human mammal according to claim 2, wherein the non-human mammal is a mouse.

9. The cell, organ or tissue according to claim 5, wherein the non-human mammal is a mouse.

* * * * *